(12) United States Patent
Wills et al.

(10) Patent No.: US 11,766,547 B2
(45) Date of Patent: Sep. 26, 2023

(54) DELIVERY SYSTEMS AND METHOD THEREOF

(71) Applicants: Thomas A. Wills, Deland, FL (US); John Addison, Eads, TN (US); Roger Cohen, Lakewood, CO (US)

(72) Inventors: Thomas A. Wills, Deland, FL (US); John Addison, Eads, TN (US); Roger Cohen, Lakewood, CO (US)

( * ) Notice: Subject to any disclaimer, the term of this patent is extended or adjusted under 35 U.S.C. 154(b) by 454 days.

(21) Appl. No.: 16/820,456

(22) Filed: Mar. 16, 2020

(65) Prior Publication Data
US 2020/0215314 A1 Jul. 9, 2020

Related U.S. Application Data

(63) Continuation of application No. 13/279,092, filed on Oct. 21, 2011, now Pat. No. 10,589,075.

(60) Provisional application No. 61/506,569, filed on Jul. 11, 2011, provisional application No. 61/405,322, filed on Oct. 21, 2010.

(51) Int. Cl.
*A61M 31/00* (2006.01)

(52) U.S. Cl.
CPC .................................. *A61M 31/00* (2013.01)

(58) Field of Classification Search
CPC .. A61M 3/0262; A61M 3/0279; A61M 31/00; A61M 35/00; A61M 35/003; A61M 35/006; A61J 7/0053; A61C 17/005; A61C 19/063; B65D 47/2012; B65D 47/2018–305
See application file for complete search history.

(56) References Cited

U.S. PATENT DOCUMENTS

| | | | |
|---|---|---|---|
| 1,622,526 A * | 3/1927 | Lewis | B65D 47/2031 222/490 |
| 1,797,686 A | 3/1931 | Homer | |
| 1,833,575 A | 11/1931 | Homer | |
| 1,836,561 A * | 12/1931 | Van Valkenburg | B65D 47/26 222/560 |
| 1,914,221 A | 6/1933 | Stewart | |
| 2,252,119 A | 8/1941 | Edmonds | |
| 3,029,003 A | 4/1962 | Erich et al. | |

(Continued)

FOREIGN PATENT DOCUMENTS

| | | |
|---|---|---|
| WO | 2008062203 A2 | 5/2008 |
| WO | 2012054878 A2 | 4/2012 |

OTHER PUBLICATIONS

Aspden P., et al., "Preventing Medication Errors," Technical Report, Institute of Medicine of the National Academies 2007.

(Continued)

*Primary Examiner* — Kami A Bosworth
(74) *Attorney, Agent, or Firm* — Scott J. Hawranek; Messner Reeves LLP

(57) ABSTRACT

An oral disposable apparatus to deliver a fluid, e.g., pharmacological agent to a patient in a one handed easy to use and sanitary manner. The apparatus includes a container capable of holding the fluid. The container is hermetically sealed with a specified quantity of fluid. A nozzle is coupled to the container. The nozzle is configured to permit comfortable insertion into a patient's mouth. An integral valve is coupled to the container and the nozzle. The valve is configured to be activated via rotation of the nozzle, thereby releasing the fluid.

12 Claims, 23 Drawing Sheets

(56) References Cited

U.S. PATENT DOCUMENTS

| | | |
|---|---|---|
| 3,116,152 A | 12/1963 | Smith |
| 3,237,817 A | 3/1966 | Dale et al. |
| 3,768,475 A | 10/1973 | Osborne et al. |
| 3,785,378 A | 1/1974 | Stewart et al. |
| 3,924,741 A | 12/1975 | Kachur et al. |
| 3,993,223 A | 11/1976 | Welker, III et al. |
| 4,096,975 A | 6/1978 | Furukawa |
| 4,112,942 A | 9/1978 | Scaife |
| 4,150,744 A | 4/1979 | Fennimore |
| 4,167,186 A | 9/1979 | Pick et al. |
| 4,405,306 A | 9/1983 | Pritchard et al. |
| 4,424,057 A | 1/1984 | House |
| 4,568,005 A | 2/1986 | Jalovec et al. |
| 4,961,924 A | 10/1990 | Suhonen |
| D356,026 S | 3/1995 | Iaia et al. |
| 5,576,083 A | 11/1996 | Agarwal |
| 5,578,020 A | 11/1996 | Mosley |
| 5,582,330 A | 12/1996 | Iba |
| 5,609,273 A | 3/1997 | Firestone et al. |
| 5,624,057 A | 4/1997 | Lifshey |
| 5,624,067 A | 4/1997 | Harwig et al. |
| 5,687,716 A | 11/1997 | Kaufmann et al. |
| D389,915 S | 1/1998 | Emerson et al. |
| D393,063 S | 3/1998 | Wefler et al. |
| 5,799,837 A | 9/1998 | Firestone et al. |
| 5,876,995 A | 3/1999 | Bryan |
| D408,450 S | 4/1999 | Kamei |
| 5,926,662 A | 7/1999 | Demaree et al. |
| 5,928,662 A | 7/1999 | Phillips |
| D412,834 S | 8/1999 | Benedict et al. |
| 6,013,750 A | 1/2000 | Friese et al. |
| 6,022,570 A | 2/2000 | Richmond |
| 6,050,399 A | 4/2000 | Pratt |
| D430,802 S | 9/2000 | Adachi et al. |
| 6,113,886 A | 9/2000 | Bryan |
| 6,199,726 B1 | 3/2001 | Cardwell, III et al. |
| 6,210,601 B1 | 4/2001 | Hottle et al. |
| 6,221,054 B1 | 4/2001 | Martin et al. |
| 6,283,933 B1 | 9/2001 | D'Alessio et al. |
| 6,367,659 B1 | 4/2002 | Seidler |
| 6,457,612 B1 | 10/2002 | Zhang et al. |
| D465,412 S | 11/2002 | Addis et al. |
| 6,485,471 B1 | 11/2002 | Zivitz et al. |
| D476,234 S | 6/2003 | Steele, IV et al. |
| D476,575 S | 7/2003 | Steele, IV et al. |
| 6,588,631 B2 | 7/2003 | Sanchez |
| D479,986 S | 9/2003 | Karim |
| D534,648 S | 1/2007 | Zahn et al. |
| D561,046 S | 2/2008 | Kerman |
| D561,586 S | 2/2008 | Hadtke et al. |
| D568,988 S | 5/2008 | Galbraith |
| D573,253 S | 7/2008 | Gonzales et al. |
| D580,274 S | 11/2008 | Abel |
| 7,457,506 B1 | 11/2008 | Osborne, II |
| D585,997 S | 2/2009 | Adam et al. |
| 7,487,894 B2 | 2/2009 | Zahn et al. |
| D588,696 S | 3/2009 | Mantle et al. |
| D590,942 S | 4/2009 | Petersen |
| D601,036 S | 9/2009 | Palmer et al. |
| D610,469 S | 2/2010 | Murray |
| D612,421 S | 3/2010 | Suero, Jr. et al. |
| 7,845,517 B2 | 12/2010 | Py et al. |
| 7,861,712 B2 | 1/2011 | Jones et al. |
| 7,874,420 B2 | 1/2011 | Coon |
| D641,469 S | 7/2011 | Ruiz, Sr. et al. |
| D643,068 S | 8/2011 | Teague |
| D645,141 S | 9/2011 | Wills et al. |
| D645,142 S | 9/2011 | Wills et al. |
| 8,020,725 B2 | 9/2011 | Yuyama et al. |
| D652,915 S | 1/2012 | Wills et al. |
| D652,919 S | 1/2012 | Sherwood et al. |
| D656,413 S | 3/2012 | Hayton et al. |
| D658,076 S | 4/2012 | Mccoy et al. |
| 8,157,464 B2 | 4/2012 | Prax |
| D677,786 S | 3/2013 | Wills et al. |
| 8,747,372 B1 | 6/2014 | Schultz |
| D725,482 S | 3/2015 | Stabinsky et al. |
| D725,483 S | 3/2015 | Abadie et al. |
| D743,273 S | 11/2015 | Anderson et al. |
| D744,856 S | 12/2015 | Stabinsky et al. |
| D745,662 S | 12/2015 | Chen |
| D753,288 S | 4/2016 | Vallotton et al. |
| D756,802 S | 5/2016 | Holbrook et al. |
| D793,547 S | 8/2017 | Burkett et al. |
| D805,164 S | 12/2017 | Norman et al. |
| D810,584 S | 2/2018 | Bystedt et al. |
| D857,192 S | 8/2019 | Burkett et al. |
| D870,270 S | 12/2019 | Burkett et al. |
| 2001/0020147 A1* | 9/2001 | Staniforth ............... A61J 7/02 604/58 |
| 2002/0097778 A1 | 7/2002 | Moroskat et al. |
| 2005/0150903 A1 | 7/2005 | Py et al. |
| 2005/0247736 A1 | 11/2005 | Mahurin |
| 2006/0019047 A1 | 1/2006 | Giori et al. |
| 2006/0108363 A1 | 5/2006 | Yates, III |
| 2007/0102662 A1 | 5/2007 | Wills |
| 2007/0228071 A1 | 10/2007 | Kamen et al. |
| 2007/0241134 A1 | 10/2007 | Gurrisi et al. |
| 2008/0065021 A1 | 3/2008 | Jenkins et al. |
| 2008/0065023 A1 | 3/2008 | Kennard |
| 2008/0147044 A1 | 6/2008 | Palmer et al. |
| 2008/0161773 A1 | 7/2008 | Holekamp et al. |
| 2009/0013994 A1* | 1/2009 | Jones ............... A61M 15/0021 128/200.23 |
| 2009/0124980 A1 | 5/2009 | Chen |
| 2009/0187194 A1 | 7/2009 | Hamada |
| 2009/0324319 A1* | 12/2009 | Houde ............. A61B 17/00491 401/138 |
| 2010/0116770 A1 | 5/2010 | Thomasset et al. |
| 2010/0239353 A1 | 9/2010 | Prax |
| 2011/0195145 A1 | 8/2011 | Moreno et al. |
| 2011/0230561 A1 | 9/2011 | Liu et al. |
| 2012/0130348 A1 | 5/2012 | Wills et al. |
| 2013/0120517 A1 | 5/2013 | Krief |
| 2017/0064994 A1 | 3/2017 | Xu et al. |
| 2017/0362000 A1 | 12/2017 | Greiner-Perth et al. |
| 2018/0029863 A1 | 2/2018 | French et al. |

OTHER PUBLICATIONS

International Preliminary Report issued in International Application No. PCT/US2011/057357, dated Mar. 6, 2014, 15 pages.

International Preliminary Report on Patenability for Application No. PCT/US11/57357 dated Mar. 6, 2014, 16 pages.

International Preliminary Report on Patentability for PCT Application No. PCT/US2011/57357 dated Feb. 25, 2014, 14 pages.

International Search report and Written Opinion issued in International Application No. PCT/US2011/057357, dated Jan. 30, 2012, 15 pages.

International Search Report for PCT Application No. PCT/US11/57357 dated Jan. 30, 2012, 3 pages.

Meller et al., "White Paper on Hospital Pharmacy Unit-Dose Acquisition and the Case for the Third-Party Repackaging Option," Center for Innovation in Healthcare Logistics, Univ. of Arkansas, Report Series 08-04, Dec. 23, 2008, 24 pages.

Meller et al., "White Paper on Hospital Pharmacy Unit-Dose Acquisition and the Case for the Third-Party Repackaging Option," Center for Innovation in Healthcare Logistics, Univ. of Arkansas, Report Series Aug. 4, Dec. 23, 2008, 24 pages.

Thompson, et al., "Unit Dose Packaging and Patient Safety," Am. J. Health-System Pharm., 2002, vol. 59, pp. 2309.

Written Opinion for PCT Application No. PCT/US11/57357 dated Jan. 30, 2012, 13 pages.

Notice of Allowance for U.S. Appl. No. 29/379,828, dated Sep. 12, 2011.

Official Action for U.S. Appl. No. 29/379,828, dated May 24, 2011.

\* cited by examiner

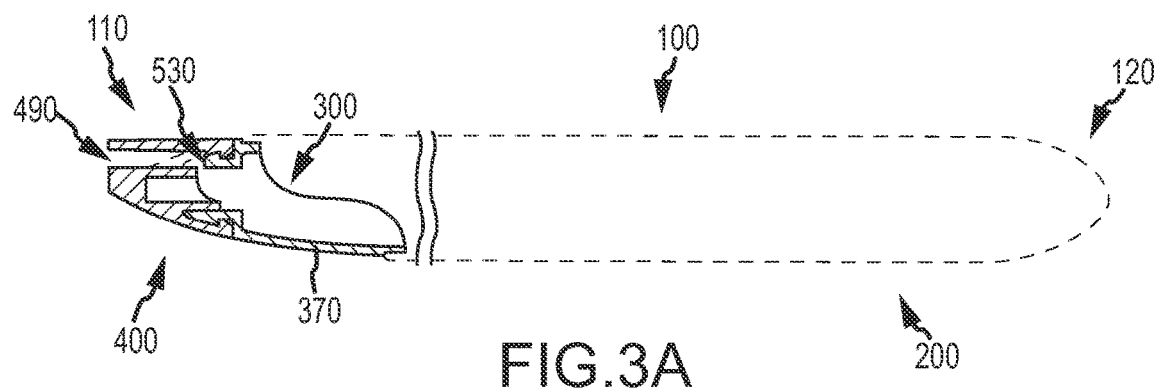
FIG.3A
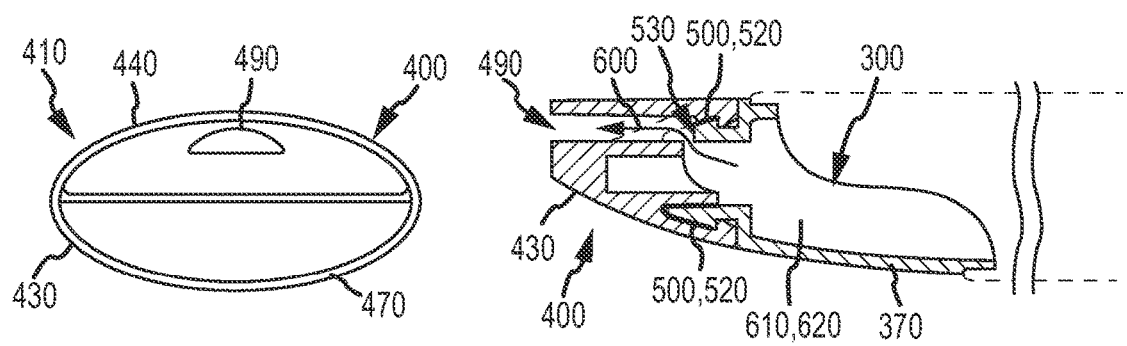
FIG.3B
FIG.3C

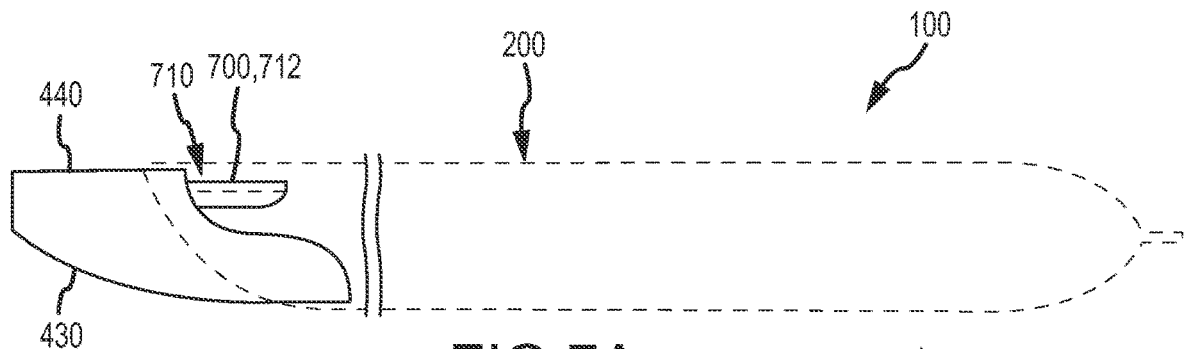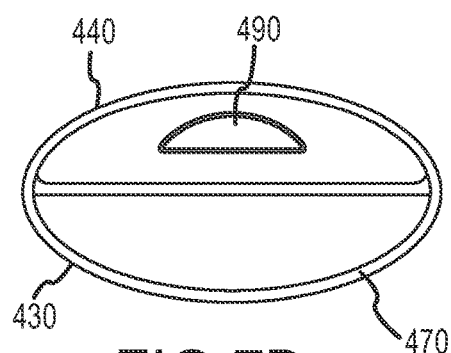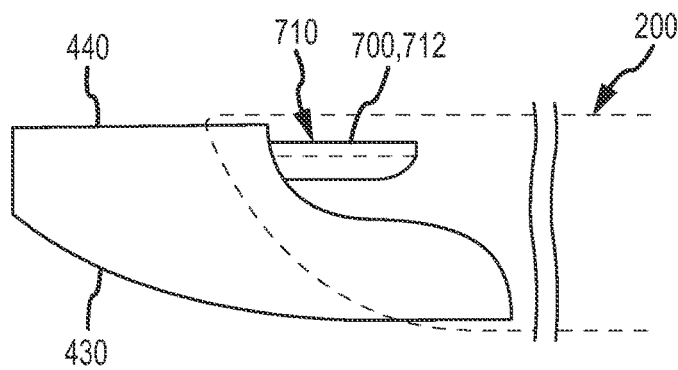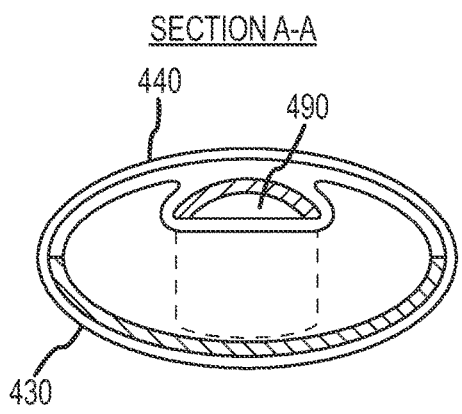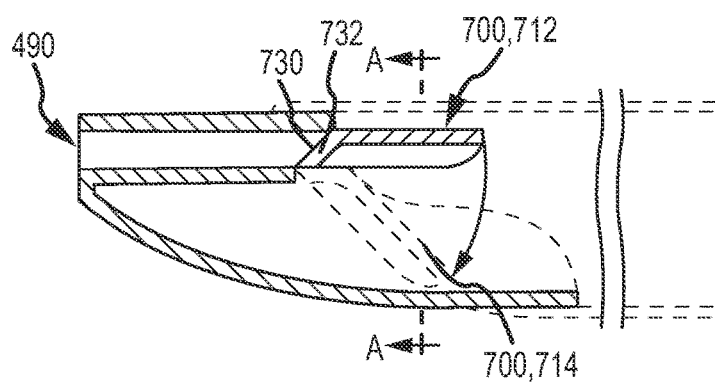

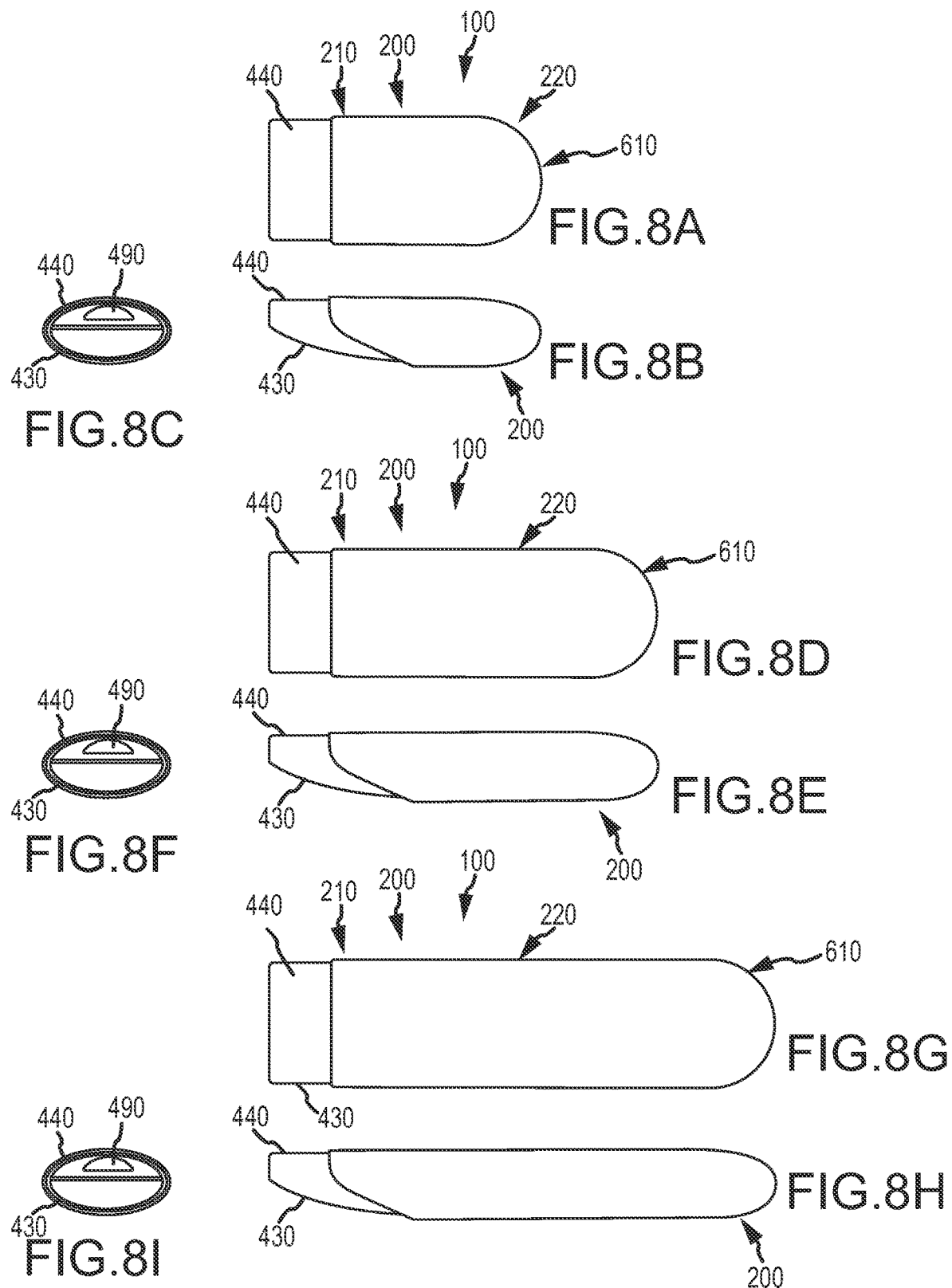

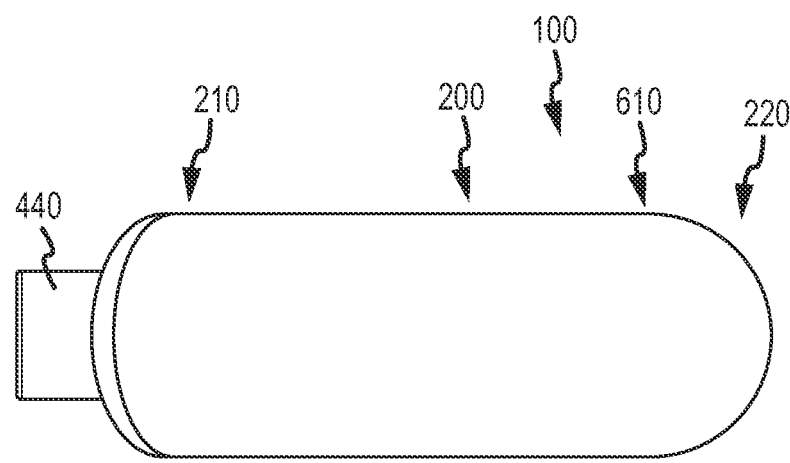
FIG.15A
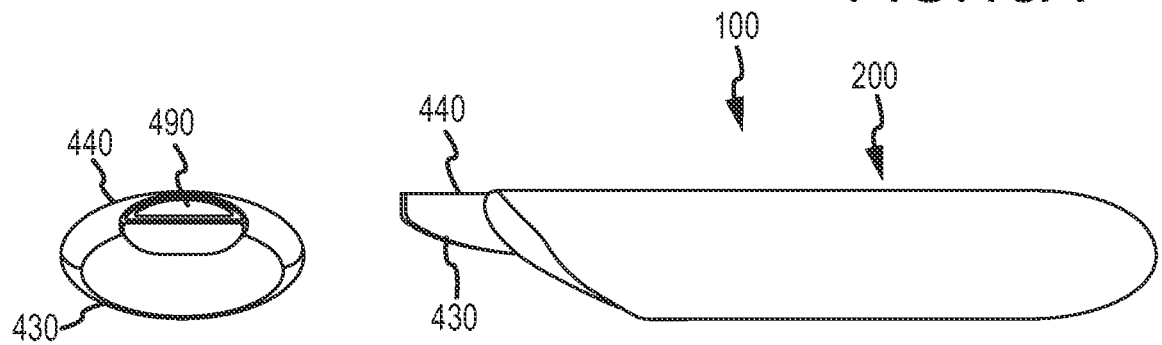
FIG.15C
FIG.15B
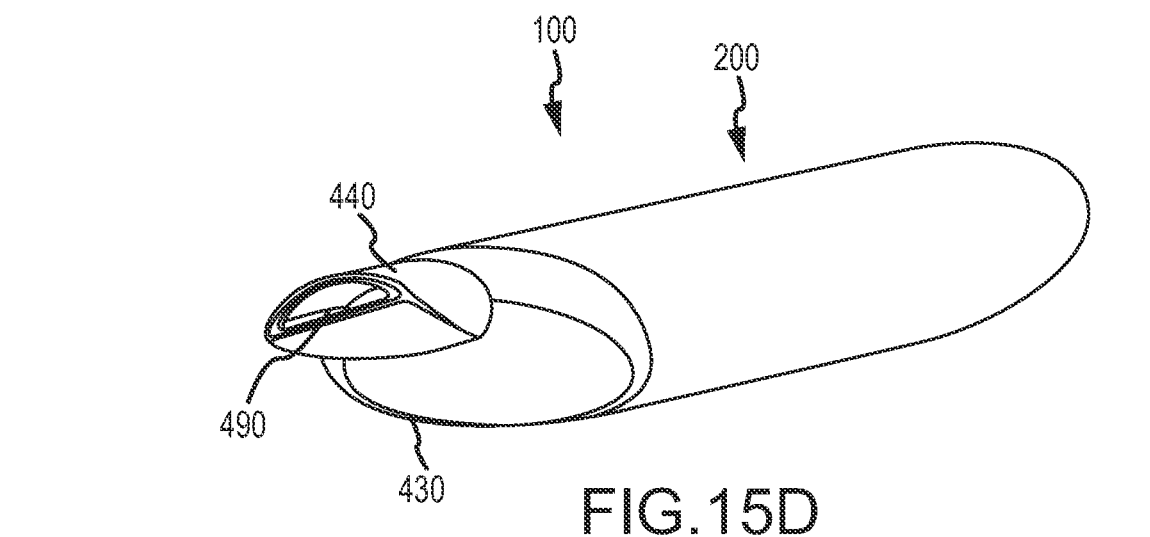
FIG.15D

DELIVERY SYSTEMS AND METHOD THEREOF

CROSS-REFERENCE TO RELATED APPLICATIONS

This application is a continuation of U.S. application Ser. No. 13/279,092, filed Oct. 21, 2011, now U.S. Pat. No. 10,589,075, which claims the benefits of U.S. Provisional Patent Application No. 61/405,322 filed on Oct. 21, 2010, and cross-references U.S. Provisional Application Ser. No. 61/506,569 filed Jul. 11, 2011, the entire content of each of the above referenced applications are incorporated herein by reference in their entireties for all purposes.

FIELD OF THE INVENTION

The present invention generally relates to delivery system, and more particularly to a device for delivery of fluids, e.g., a product delivery system containing liquids, creams, ointments and gels for, but not limited to, the medical, pharmaceutical, health and beauty, food and beverage, consumer products, veterinary, and automotive industries. Examples include delivery of a pharmacological agent, e.g., liquid acetaminophen (Tylenol), liquid ibuprofen (Advil), liquid antacid (Maalox), liquid cough and cold medicines, and many others.

BACKGROUND OF THE INVENTION

One of the most convenient methods of administering medicine in small amounts is to package the medicine in a pre-filled, pre-determined amount. This not only makes the administering of the medicine easier, but also helps insure against accidental over-dosing. Unfortunately, many medicines are still packaged and stored by older, conventional means. If there were some way of packaging, storing and administering low-dose medicine, in an easy-to-use manner, it would be beneficial to many people.

In hospitals today, there is a high demand for pre-packaged unit-doses for all liquid "over the counter" ("OTC") medicines and liquid drug products. A paper by the Center for Innovation in Healthcare Logistics published Dec. 23, 2008, stated that "the option preferred by 85% of hospital pharmacy directors is to purchase medications directly from the manufacturer in unit-dose form." Some liquid medications are available to hospital pharmacists in pre-packed unit doses, but these packages are generally multiple piece parts that are primitive and somewhat awkward. In addition, many hospitals today actually make their own unit doses from larger bottles by hand, one at a time, in the pharmacies themselves, or hire yet another company to do this service for them. Compared to all of these options available to hospital pharmacists, a Unit-Dose Delivery Systems ("UDDS") for liquids, creams and gels solution is not only more efficient, but it is also safer, reduces potential errors, provides a longer shelf life, and will be less expensive in most instances.

Liquid medicine doses are typically administered using one of four measured quantities: teaspoon, cup, dropper or syringe. The dosing amounts are listed on a table located on the outside of a carton or the device for a given age and/or weight of a person, with the table normally specifying the correct dose. Because of differing methods of administration and the range of doses, the tables can be difficult for the end user to understand. The traditional four delivery methods used for oral medications are as follows:

A spoon is the most traditional method of delivery where the user fills the spoon with the prescribed amount of liquid and inserts the spoon into a patient's mouth. The advantage of this method is that spoons are convenient. A disadvantage is that spoons are shallow, thus making it difficult to not spill the liquid when pouring out the proper amount. Also, a spoon is imprecise as to measurement. Perhaps more importantly, it may be very troublesome to convey the liquid into an unwilling child's mouth without spilling at least some or all of the medication in the process.

Sensing the need for a delivery method that allows administering medication away from the home, manufacturers began marketing products that included a plastic cup with the packaging of the medication. The plastic cup included calibration marks corresponding to the recommended doses and could be reused after washing. The advantage of this system is that it may be used at any location, it is accurate, neat to use, and simple to understand. The downside is that after use the cup may have a coating of medication on the inside and must be washed, this may be problematic if there is no water available at the time. Further, if the cup is not cleaned expeditiously, the remaining contents could become sticky and hard to clean. Another disadvantage is the potential for cross contamination from one user to another. Also, it is commonly difficult to read the gradations of volume, and are hard to transport.

The dropper method is often used for administration of liquid medicine to infants or small children. The dropper shaft is usually marked for the dosage, for ease of filling from a bottle. The dropper is then placed in the patient's mouth and the bulb is squeezed to release the medication. The dropper is washed and is either placed into a carton or a medication bottle for storage. One advantage is that infants and small children may not be able to drink liquid from a cup therefore, medication may be easily released directly into their mouth. Another advantage is that this method may be used to administer medication to those who may have difficulty in taking pills. The downside is that droppers are difficult to sterilize using tap water exclusively and cross contamination is probable, particularly since the dropper must be inserted into the medication, sometimes multiple times, to obtain the proper dose. Further difficulty can arise when filling the dropper if the bottle is almost empty.

The dropper method has received increasing interest. Many liquid dispensers of the squeeze-bottle type have been developed for dispensing medicinal solutions in droplet form. Most conventional dispensers include a container formed from a resilient plastic material having an opening therein for producing drops of liquid which are dispensed from the container upon squeezing thereof.

Syringes also are used to administer liquid medicine. Disadvantages of syringes include inaccuracies in measurement and difficulty of use. An advantage is that syringes are well-known devices, especially in hospital environments.

Medications are often prescribed which must be dispensed in a metered amount over a predetermined period of time. The medication is typically packaged and marketed in containers enabling individual self-administrable dosages and the user typically self-administers the medication over a predetermined period of time. This is often the case in the field of ophthalmology wherein various forms of medication are frequently prescribed for the patient to be dispensed in metered drops from a disposable container. Any number of medications may be administered in this manner and such medications typically include decongestants, antibiotics, anti-inflammatories, anti-glaucomic medication, antibacterials, anesthetics, mydriatics, anti-cholinergics, antibiotics as well as combinations thereof.

Since the dispensed drops are to be metered, it is important that a predetermined volume of solution is dispensed per drop, and it is important that only one drop be dispensed per squeeze of the container. Naturally, the dispenser must be suitable for providing multiple doses or drops from a single container, and each of the drops must be of equal size.

Toward providing a predetermined medication, disposable pre-filled containers have been developed. For example, a pre-filled medication may be provided in a disposable plastic container, such as a pipette, dropper or other similarly shaped device to orally administer the liquid medication. The container may be sized to accommodate a specific amount of medication for oral administration in one dose.

Some liquid medications are available to hospital pharmacists in pre-packed unit doses, but these packages are generally in multiple piece parts that are primitive and somewhat awkward. In addition, many hospitals today actually make their own unit doses from larger bottles by hand, one at a time, in the pharmacies themselves, or hire yet another company to do this service for them. Compared to all of these options available to hospital pharmacists, a Unit-Dose Delivery Systems ("UDDS") for liquids, creams and gels solution is not only more efficient, but it is also safer, reduces potential errors, provides a longer shelf life, and will be less expensive in most instances.

In one embodiment of the invention a UDDS is disclosed. Traditional medical delivery systems are deficient in a variety of ways. For example, the devices include and/or require disposable parts which may present a choking hazard to small children and the elderly, provide inaccurate dosage, are difficult to operate, may be cost prohibitive, and/or are of limited shelf life.

By way of example, Phillips in U.S. Pat. No. 5,926,662 ("Phillips") teaches a drug delivery device that has a reservoir holding medicine for delivery to a patient. The device has a conduit with one end coupled to the reservoir and a free end to position within the fornix of a patient's eye. Through gravity and capillary action, the medicine flows into the eye with a rate of delivery adjusted according to the size and material of the conduit. The invention has the reservoir made of an absorbent material provided with an impermeable backing which acts as a barrier. In the preferred embodiment, the backing has an adhesive for attaching to the eye of the patient. Phillips is incorporated by reference in its entirety for all purposes.

U.S. Pat. No. 5,799,837 issued to Firestone, et al. ("Firestone I") is for a packaged pharmaceutical product having an extended shelf life and includes a container consisting of a hollow body with an open end. The body wall thickness enables drop-by-drop dispensing of a medicine by manually squeezing the container body. A tip is fixed to the body to form droplets for application. Firestone I is incorporated by reference in its entirety for all purposes.

Lifshey in U.S. Pat. No. 5,624,067 ("Lifshey") discloses an ophthalmic storage and dispensing device formed by injection molding, consisting of a vial with thick rigid walls and a limited flexible area. The flexible area allows only a small displacement when squeezed, providing a metered volume of liquid. The tip has a integral-molded puncture membrane to provide sealing. Lifshey is incorporated by reference in its entirety for all purposes.

Firestone, et al. in U.S. Pat. No. 5,609,273 ("Firestone II") teaches a barrier package that includes a container with a hollow body and an open end having a body thickness which enables a drop-by-drop dispensing of a medicant by manually squeezing the container. A dropper tip is fixed to the open end and forms droplets upon manual squeezing of the body. Firestone II is incorporated by reference in its entirety for all purposes.

U.S. Pat. No. 5,578,020 issued to Mosley ("Mosley") is for an eye drop dispenser and dispensing sleeve. The dropper has a liquid reservoir portion and a dispensing end with a dropper orifice. Part of the reservoir is resilient and a dispensing sleeve circumscribes the dropper tube with a pair of legs that extend beyond the end of the tube. The legs are adapted to fit against the orbital areas of an eye to support the dropper over the eye for application of the liquid. Mosley is incorporated by reference in its entirety for all purposes.

Fennimore in U.S. Pat. No. 4,150,744 ("Fennimore") discloses a packaging device for light and oxygen sensitive liquid which includes a dropper spout. The vessel itself is sealed within a gas impermeable envelope under vacuum. Fennimore is incorporated by reference in its entirety for all purposes.

U.S. Pat. No. 7,487,894 issued to Zahn et al. on Feb. 10, 2009 ("Zahn I") and U.S. Pat. No. D534,648 issued to Zahn et al. on Jan. 2, 2007 ("Zahn II") teach a dispensing container fillable with a liquid including a squeezable reservoir for holding the liquid prior to dispensing; a dispensing head which appears substantially flat in profile and which is integral with the squeezable reservoir and having a distal end and a proximal end and having a bottom surface and a top surface one or both of which has an indented portion; an outlet at the distal end of the dispensing head for dispensing the liquid from the container; a passage interconnecting the squeezable reservoir and the outlet; and a stop disposed near the proximal end of the dispensing head to prevent over-insertion of the dispensing head into a user's mouth when the container is used to dispense the liquid to the user. Containers that are pre-filled with liquid and a method of making the containers are also described. Zahn I and Zahn II are incorporated by reference in its entirety for all purposes.

U.S. Pat. No. 6,457,612 issued to Zhang et al. on Oct. 1, 2002 ("Zhang") teaches an improved pre-filled disposable pipette consisting of a hollow tube dimensioned to enclose a medicinal product and having attached a medication transfer tube from where the pipette is filled and the medicinal product released. The improvement consists in having a primary grasping tab attached to an upper end of the bulb; a secondary grasping tab attached to each side of the tube; and a support tab also attached to each side of the tube near the lower end of the tube. The primary and secondary grasping tabs allow the pipette to be conveniently and easily handled without having to grasp the sensitive bulb or to directly grasp the tube. The support tab functions to allow the pipette to be placed on a conveyor rack apparatus from where the pipette can be automatically filled and sealed by a cap or heat applied foil. Zhang is incorporated by reference in its entirety for all purposes.

U.S. Pat. No. 2,252,119 issued to Edmonds et al. on Aug. 12, 1941 ("Edmonds") teaches a design for a dispensing container. The Edmonds design features and requires a break-away tab that separates from the rest of the device. The tab must be removed to dispense the fluid contained in the device. Edmonds is incorporated by reference in its entirety for all purposes.

U.S. Pat. No. 3,993,223 issued to Welker et al. on Nov. 23, 1976 ("Welker") teaches a sealed dispensing container for liquid medicaments is described which may be readily opened by a twisting force applied on opposite ends of the container. All of the parts of the container making up a chamber for the medicament are shaped to be substantially completely flattened by the application of a compressive force, such as that applied by thumb and forefinger, to completely discharge the liquid medicament. After the container is opened, the liquid will be retained in the container in the absence of a compressive force and regardless of the orientation of the container in a horizontal or inverted position. Welker is incorporated by reference in its entirety for all purposes.

International Pub. No. WO 2008/062203 published to Mcaffer et al. on May 29, 2008 ("Mcaffer") teaches an ampoule made of plasties material, for liquid or suspension pharmaceuticals, has a reservoir linked to a removable head by a channel in a neck portion. The channel has a trap, thus located between its reservoir and the head, in the form of an elongated restriction and/or a bend to trap liquid or suspension which may settle during storage, and prevent either reaching the head. Mcaffer is incorporated by reference in its entirety for all purposes.

As mentioned, traditional medical delivery systems are deficient in a variety of ways. For example, the devices include and/or require disposable parts which may present a choking hazard to small children and the elderly, provide inaccurate dosage, are difficult to operate, are cost prohibitive, and/or are of limited shelf life. Therefore, there is a long-felt need for an efficient single-use delivery system for liquids, creams and gels. The delivery device is cost efficient and requires no detachable parts.

SUMMARY OF THE INVENTION

Accordingly, the invention is directed to a delivery system and method thereof that substantially obviates one or more of the problems due to limitations and disadvantages of the related art.

An advantage of the invention is to provide an apparatus with an extended shelf life of at least one year or more.

Yet another advantage of the invention is to provide an apparatus that has a degree of safety and does not include choking hazards, e.g., does not include removable components, such as caps, tabs, etc. Other safety features may include a cap that can be closed, e.g., single use device.

Still yet another advantage of the invention is to provide an apparatus that is easy to use for people with normal dexterity or reduced dexterity, e.g., one handed operation for people of normal dexterity, easy use operation for people with reduced dexterity.

Another advantage of the invention is to provide an apparatus having a tube that can be filled from either end.

Yet still another advantage of the invention is to provide an apparatus that can accommodate multiple components for use in medical, pharmaceutical and consumer products.

Another advantage of the invention is to provide an apparatus that can be used orally.

Still yet another advantage of the invention is to provide an apparatus that is inexpensively manufacturable, e.g., injection molded, blow molded, and the like.

Another advantage of the invention is to provide an apparatus that has a portion configured for spreading lotions and creams, e.g., a cap portion with an angled portion for spreading.

Still yet another advantage of the invention is to provide an apparatus that can be tracked with tagging and tracking features, e.g., RFID tags, and the like.

Yet still another advantage of the invention is to provide an apparatus that is a single use disposable apparatus or multiple use product.

Still yet another advantage of the invention is to provide an apparatus that can accommodate a wide range of volumes, e.g., 2 mL to 500 mL dosing, thereby allowing for precision dosages of pharmaceuticals.

Additional features and advantages of the invention will be set forth in the description which follows and, in part, will be apparent from the description, or may be learned by practice of the invention. These features and other advantages of the invention will be realized and attained by the structure particularly pointed out in the written description and claims hereof, as well as in the appended drawings.

Certain embodiments of the present disclosure relate to a delivery system device, and more particularly to a system for delivery of fluids, e.g., a product delivery system containing liquids, creams, ointments and gels for, but not limited to, the medical, pharmaceutical, health and beauty, food and beverage, consumer products, veterinary, and automotive industries. In one embodiment, anti-fungal ointments or hand sanitizer are included. The delivery device, also known as an oral disposable apparatus, delivers a fluid, e.g., pharmacological agent, to a patient in a one handed easy to use and sanitary manner. Any fluid or semi-solid material may be used in this apparatus. By way of further illustration, food products may be included, such as energy drinks, chocolate, spirits (alcohol), and the like. In one embodiment, the apparatus includes a container capable of holding the fluid. The container includes a seal that allows an extended shelf life with a specified quantity of fluid. A nozzle is coupled to the container. The nozzle is configured to permit comfortable insertion into a patient's mouth. An integral valve is coupled to the container and the nozzle. The valve is configured to be activated or engaged via rotation of the nozzle, thereby releasing the fluid. Creams and gels can be expelled directly into the user's hands or directly onto an application surface and spread with spreading surface. For liquids to be taken by mouth, the end is designed to comfortably fit between the lips of adults and children alike, so the user can simply insert the open end into his or her mouth and squeeze or lightly draw with suction the contents from the package.

Other embodiments and alternatives to this device are described in greater detail below.

As used in this disclosure, the term "device" and "delivery device" all refer to one or more embodiments of the invention. Also, the term "tube" refers broadly to a substantially hollow component, fluid reservoir, with one or two ends, that may have any of a variety of different geometric shapes, to include a cylinder of various cross-sections such as circular, oval, oblong and rectangular, a pillow shape to include a clam-shell or dome-like shape, and shapes of irregular cross-section such as those of wavy-profile. The terms "cap" and "nozzle" refer to the cap component of the device. The phrase "removably attached" and/or "detachable" is used herein to indicate an attachment of any sort that is readily releasable.

Briefly, in one preferred embodiment of the invention, the device is generally configured in a cylinder tube configuration with a twist opening feature. The device generally has a device first end and a device second end. Further, the device comprises a tube, a neck, and a cap. The tube section comprises a tube first end, a tube second end, a tube upper end, and tube lower end. In addition, the tube comprises a tube exterior surface, tube interior surface, and tube thickness. The neck portion of the device comprises a neck first end, a neck second end, a neck upper end, and neck lower end. The cap section of the device comprises a cap first end, a cap second end, a cap exterior surface, and a cap second exterior surface. Furthermore, the cap includes a cap fluid discharge opening. Upon twisting the cap section, a fluid discharge channel is created, which enables fluid to be discharged from the device.

In a preferred embodiment, the tube portion of the device is configured to engage a neck portion, which in turn engages a cap portion. A seal is provided that is inserted between the cap and neck. The seal may be a mechanical seal, viscous fluid seal and combination thereof. In a preferred embodiment, the seal includes a material such as nitrile rubber, thermoplastic elastomers, silicone and combinations thereof. The tube is configured to contain a fluid, and the cap has a fluid discharge opening. When engaged, the seal, in a preferred embodiment, provides a seal configured to allow for an extended shelf life, e.g., 1 year or more and more preferably 2 years or more, between the exterior of the device and the fluid contained within the device. In a more preferred embodiment, the seal is configured as a hermetic seal. In one embodiment, the device does not have a hermetic seal.

In one embodiment, the device is a container closure system.

In one embodiment, the cap, neck, and tube features combine or are one integral element.

In one embodiment, the cap, neck and tube are coupled with at least one of a snap fit, interference fit and combinations thereof. That is, any of the neck, cap or tube can be coupled with any combination of an interference fit or snap fit.

In one preferred embodiment of the device, the cap section may be twisted in only one direction, either clockwise or counterclockwise (when viewing the device from its first end). In another embodiment, the cap may only be twisted to a maximum of approximately 180 degrees. In another embodiment, the cap may be twisted in either a clockwise or a counterclockwise direction, and may or may not be unidirectional. In another embodiment, the device, when twisted to its maximum range, locks in place. Regarding the range of motion of the cap, the range of rotation is typically at least about 180 degrees, more typically approximately 180 degrees, and even more typically at least about 170 degrees.

In one preferred embodiment of the neck portion of the device, the neck portion comprises a neck thickness and the cap comprises a cap first end, cap first exterior surface, a cap second exterior surface, cap thickness, and cap fluid discharge opening.

In another embodiment of the device, the seal, when first positioned to either the neck or the cap, is of a first thickness, and then, upon engagement with the other of the cap or neck, reduces to a second thickness.

In one embodiment of the invention, the neck portion, in the area in which engagement with the cap occurs, includes a neck alignment ridge, and the cap, in the same area of engagement, includes a cap alignment grove. The neck alignment ridge engages the cap alignment grove to provide a secure connection between the cap component and the neck component. In one embodiment, a seal is provided in the engagement area between the neck alignment ridge and the cap alignment grove.

In one preferred embodiment, the device is generally of a cylindrical cross-section and each of the tube, neck and cap are substantially aligned along a central axis, that is, they are aligned axially.

In one embodiment, the tube may be filled from its second end, that is, the end that is not connected to the neck portion. Subsequently, the end may be sealed with a thermal process, glue, or other attachment means as known in the art.

In one embodiment, the tube portion of the device is extended to hold a precise volume of fluid, for example, the tube portion can be sized to a volume in range from about 5 mL to about 50 mL or greater. For example, the tube portion can have a volume, such as 5 mL, 10 mL, or 15 mL. The size of the device and its ability to contain varying degrees of fluid content are enabled by extension of the tube portion. Varying degrees of elongation of the tube section allow for varying levels of fluid containment area and therefore varying amounts of fluid content volume. Regarding the range of volume the device may hold, the range of fluid volume for a single-use application for a medicinal fluid is typically between about 1 ml, to about 100 mL, more typically between about 5 mL to about 80 mL, and even more typically between about 5 mL and 50 mL.

In another embodiment, the device is scalable, that is, components of the devise may be increased or decreased in size in a substantially proportional manner.

In another embodiment, the device includes a tube portion with a fracture tab opening feature. This embodiment includes a tube, cap first exterior surface, cap second exterior surface, and fracture tab with fracture tab pressing point and fracture tab position one and fracture tab position two. Further, the device includes a cap second exterior surface, cap first exterior surface, and cap thickness. In this embodiment, when a user depresses a portion of the tube by applying a substantially downward vertical force at a fracture tab pressing point, the fracture tab depresses and thereby allows fluid to discharge from the device. When the fracture tab is in its fracture tab position one, fluid is unable to discharge from device through cap fluid discharge opening. However, when a user engages device by pressing hinge at fracture tab pressing point, the hinge rotates downward to the position of fracture tab position two, thereby allowing fluid to emit through cap fluid discharge opening.

In one preferred embodiment of the invention, the tube is configured as a clam-shell or dome shape and the device is of one integrated portion, that is, the neck, cap, and tube are not separately identifiable and appear as one integrated unit.

One embodiment of the device includes a hinged fracture tab feature. The hinge, when in fracture tab position one, is substantially planar and, when pressed (so as to allow fluid to be emitted from the device), it rotates downward to approximately 45 degrees. This configuration of the hinged fracture tab is preferred for tube shapes that are other than clam-shell or dome shaped, such as cylindrically-shaped tubes.

In another embodiment of the hinged fracture tab feature, the hinge, when in fracture tab position one, is substantial raised upwards and, when pressed (so as to allow fluid to be emitted from the device), rotates downward through a radial distance of approximately 90 degrees. This configuration of the hinged fracture tab is preferred for shapes such as clam-shell or dome shapes.

In another embodiment, the hinged fracture tab feature rotates through a ratial distance of approximately 45 degrees. This configuration is preferred for tube shapes substantially not a dome shape, to include cylindrical shapes.

Regarding the range of nominal position of the fracture tab in fracture position one in this embodiment, the range of fluid volume is typically in a range from about 75 degrees to about 15 degrees, more typically in a range from about 60 degrees to about 30 degrees, and even more typically in a range from about 50 degrees to about 40 degrees.

Regarding the range of motion of the hinged fracture tab, the range of rotational motion is typically in a range from about 0 degrees to about 90 degrees, more typically in a range from about 0 degrees to about 60 degrees, and even more typically in a range from about 0 degrees to about 45 degrees.

In one embodiment, when a user presses on the tube upper end so as to engage fracture tab with sufficient pressure to push fracture tab downward, a tab rotates within the device tube and the fracture tab rotates to its fracture tab position two so as to allow fluid contents contained in the fluid containment area to be discharged through cap fluid discharge opening.

In another embodiment of the invention, the device is configured with a slider mechanism to enable opening and closing of the device. In this embodiment, the device is generally configured in an oval cylinder tube configuration with a slider opening feature. The device generally includes a tube, a neck, and a cap. The tube section includes a tube first end and a tube second end. The neck includes a neck first end. The cap section of the device includes a cap first end and a cap second end. Furthermore, the cap includes a cap fluid discharge opening.

The slider mechanism is configured to traverse relative to the neck portion such that a fluid discharge channel is created from the tube interior to the cap fluid discharge opening. When the slider mechanism is configured such that when the cap second end is flush-with and/or in contact with the neck portion, the device is closed and unable to discharge its fluid contents. This is the closed device position or position one. When a force is imparted in a direction substantially away from, that is from the cap second end toward the cap first end, the slider mechanism moves out from the device (and thus the device becomes longer in length) and fluid discharge channel is created, thereby enabling fluid to be discharged from the device.

In a preferred embodiment of the device configured with a slider mechanism, the device allows an extended shelf life of the fluid contained within the device.

In a preferred embodiment of the device configured with a slider mechanism, the device has not detachable parts or components or elements.

In a preferred embodiment of the device configured with a slider mechanism, the device includes an indent substantially near the exterior interface between the cap and neck. The indent may be configured as a channel on the upper and/or lower portion of the cap at the cap second end and/or the upper portion of the neck at the neck first end. The indent may be configured to assist the user in opening and/or closing the device.

In a preferred embodiment of the device configured with a slider mechanism, the device slides 0.125 inch forward to open, and/or an internal lock prevents the cap from detaching from the device.

In one embodiment of the device configured with a slider mechanism, the device is at least one of hermetically sealed or airtight sealed.

In one embodiment of the device configured with a slider mechanism, the slider mechanism is a plunger mechanism as known to one skilled in the art.

In one embodiment of the device configured with a slider mechanism, the device includes some or all internal mechanisms and/or features substantially as described previously for the twist opening feature.

In another embodiment of the device configured with a slider mechanism, the device includes some or all internal mechanisms and/or features substantially as described previously for the hinged fracture tab feature.

In another embodiment of the device configured with a slider mechanism, the device may optionally include a seal, fitted between the neck and cap interconnection area.

In another embodiment of the device configured with a slider mechanism, the device may be filled with fluid from either its second end (the end opposite to the cap fluid discharge opening) or from the device's first end, that is into the fluid discharge opening.

In a preferred embodiment, a pre-filled oral, topical spreading or general dispensing container includes a soft and flexible plastic tube to contain fluids and is bonded and sealed to a hard plastic nozzle. Filling of fluid into the variable length tube occurs at an open end or separate opening, and then sealed by conventional fill and seal equipment. The nozzle, fluid channel, and fluid control valve can be increased or decreased in scale to accommodate various tube or container volumes and rates of flow that can be released under pressure of the manual activation. Fluid is released by applying manual pressure with thumb or finger thru the flexible tube and the nozzle cut-out opening onto the tab in a downward motion toward the stationary plane held in place by the opposing thumb or finger. The tab fractures away completely at the top and side perimeter fracture line away from the nozzle and bends at the hinge line so as to keep the tab attached to the body (10). The fracture/bend event is possible because the tab motion at the fracture line moves from either a general seal that allows for an extended shelf life or hermetic seal closed position in a descending arc of movement to about 0 degrees of no movement at the hinge line to a full open position. This releases the fluid from the containment area through the fluid channel into the mouth, onto the receiving surface or other desired location.

In a preferred embodiment of the device, the device and none of its component parts are detachable.

In a preferred embodiment of the device, the seal is a hermetic seal.

In a preferred embodiment of the device, the seal allows for an extended shelf life, e.g., 1 year or more and more preferably 2 years or more, and the fluid within the device does not expire for a period, measured from date of filling, of at least 1 year.

In a preferred embodiment of the device, the seal allows for an extended shelf life, e.g., 1 year or more and more preferably 2 years or more, and the fluid within the device does not expire for a period, measured from date of filling, of at least 2 years.

In another embodiment, the device includes an identification tag, such as a Radio Frequency Identification Device (RFID), a bar code, a magnetic strip, and combinations thereof. The identification tag may be active (that is, emits a signal and/or energy) or passive (that is, it does not emit any signal or any energy).

In another embodiment, the device includes a fluid status indicator, such as a fluid expiration status, fluid volume status, fluid type and combinations thereof.

In a preferred embodiment, the device is constructed from a material including at least one of polycarbonate, polyethylene, polyester, polystyrene, polypropylene, polysulfone, polyurethane, and ethylene-vinyl-acetate.

In a preferred embodiment, at least one of the tube portion, the neck portion, and the cap portion comprise a material selected from the group consisting of polycarbonate, polyethylene, polyester, polystyrene, polypropylene, polysulfone, polyurethane, ethylene-vinyl-acetate and combinations thereof.

In another embodiment, the tube portion comprises a material of lesser hardness than a material contained within at least one of said neck portion, cap portion, and seal portion.

In another embodiment, the fluid contained in the tube comprises a pharmacological agent and/or a medicament, for example, any of liquid acetaminophen (Tylenol), liquid ibuprofen (Advil), liquid antacid (Maalox), liquid cough and cold medicines.

In another embodiment, the fluid contained in the tube comprises health and beauty products, energy boost products, veterinary care products, dental products to include local anesthetic used in dentistry, such as Novocain and Lidocaine. The fluid may also contain any substance were precision volumes are to be delivered, to include explosives and adhesives.

In a preferred embodiment, the device may be operated by a user with a single hand and/or by the elderly and/or without external light.

In another embodiment, the device is one of translucent, transparent, reflective, and glows-in-the-dark.

In another embodiment, the device is manufactured by injection molding, to include as a one piece device or in its component parts (to include the cap, neck and tube). The device may also be manufactured using a wide variety of methods, such as blow-fill-seal, vacuum chamber liquid filling, extrusion and other methods well known in the art.

In a preferred embodiment, the device may be custom molded to contain a specific volume, e.g. 7.25 ml.

In another embodiment, the device provides a tactile and auditory response upon fracture of the fracture tab.

In a preferred embodiment, the cap and/or the device first end is ergonomically designed and/or manufactured with smooth lines and contours and no rough edges to enable a smooth interaction with a user's mouth/receiving area.

In another embodiment, the device has a specific color, thereby indicating the type of liquid medication contained within. Color pigment is added to the exterior on the material itself when fabricated and may otherwise be substantially transparent or translucent. It should be noted that the container color represents a specific medication, thus permitting the medication within the container to be colorless and yet recognizable by the user. It should be noted that in today's pharmaceutical industry, particularly for over-the-counter types of medicine, color plays an important role in identification of a product. Thus, by permitting the color to be integral with the device/container, instead of the medication, a benefit is provided. It should be further noted that even an empty colored container still retains its identity.

Although well suited for use in human patients, and although much of the discussion of the present invention is directed toward use in humans, advantages offered by the present invention may be realized in the veterinary and scientific fields for the benefit and study of all types of animals and biological systems. It should be appreciated, however that the principles of the present invention can also find application in other areas, specifically where there is a desire to deliver precise amounts of fluid material to particular regions.

As one skilled in the art would appreciate, the device cross-section need not be limited to the shapes described above. For example, cross-sections of an oval shape or those with at least one defined angle to include obtuse, acute, and right angles can provide a shape in some situations that is more congruent with the application and/or dispensing of the fluid. A substantially round shape may also be employed that provides the user with an indication of directional orientation.

According to various embodiments of the present disclosure, it is an aspect of the present invention to provide a device having at least one hollow tube adapted to enclose a fluid product devoid of any grasping tabs that may undesirably complicate manufacturing and use, and including embodiments where the hollow tube is not easily deformed; is not re-sealable after use (e.g. is particularly for a "one use only" application) and is not filled while in a hanging position from any grasping tabs, like other prior art devices.

In another embodiment, the invention may also be used multiple times due to the open and closed nature of the nozzle.

In other embodiments, the device includes a reservoir, a chamber which is in fluid communication with the reservoir and an outlet that is operable by a person's mouth to sever the chamber from the reservoir, with certain embodiments where the reservoir is not completely filled with non-compressible fluid, such as the medicating liquid, so as to prevent breakage under certain environmental conditions.

In still other embodiments, a pre-filled oral liquid disposable plastic container is provided to deliver medication to a patient in an easy to use and sanitary manner utilizing a pre-determined quantity of liquid medication pre-filled into the container with the container sized appropriately. In certain versions, the container is substantially clear and medications are colored so that a consumer can determine what amounts are inside, if the device has been used, etc. In certain embodiments, markings are present on the container to gauge and provide indicia of how much material is present.

In preferred embodiments, the device is devoid of any metal containing features that would trigger, for example, security alarms at airports, etc. Specifically, preferred embodiments do not employ any metallic foil closure for sealing the liquid medication within and do not rely upon any tab to remove a seal. Certain embodiments are directed to a disposable container having at least one generally flexible plastic body containing a precise dose of the medicament to be dispensed but that does not employ a tab portion that must be manipulated by a consumer to provide an opening for dispensing the container contents. Instead, the device is designed such that a consumer can operate it to obtain a dose of medication simply using one hand and without requiring the manipulation of tabs for release of medicants.

In certain embodiments, the body itself is made from material that has substantially the same flexibility (while possibly differing in plastic composition throughout) and can be of a shape and size such that it is not necessary to have a user grasp particular portions to open the device in use. Preferred embodiments do not employ a cap for fitting over orifices, which only increase the expense of manufacture and diverges from the single-use-only aspects of certain embodiments. Still other embodiments are directed to an oral medicine dispenser for the administration of a single pre-measured dose, which dispenser comprises a body having a collapsible or semi-collapsible reservoir portion and an elongated dispensing tube portion extending from the reservoir portion. The contents of the single dose of a fluid oral medicament is preferably released by manipulating, e.g. solely via one's mouth, a collapsible reservoir portion to dispense the medicament dose, with other embodiments having suction-reducing features to permit the entire amount of the medicine to be sucked from the device (e.g. a port that permits air to enter the device to assist mendicant to be sucked into one's mouth). Therefore, embodiments of the invention are directed towards unit dose delivery systems that substantially obviate one or more of the problems due to limitations and disadvantages of the related art.

In certain embodiments, an advantage of the invention is to provide an apparatus operable with one hand, e.g., the apparatus can be activated with manual pressure of a thumb or finger or via one's lips. Another advantage of the invention is to provide an inexpensive disposable apparatus.

An embodiment of the invention is directed toward a liquid delivery apparatus, e.g., a unit dose delivery system. The delivery apparatus may be manufactured in many sizes, e.g., from about 1 mL to about 50 mL or greater, and can be packaged together in many different ways to suit a breadth of customer needs. In a preferred embodiment, all sizes are a single piece injection molded part with smooth lines and contours, no rough edges, where one end glides into the user's mouth and, with a single press in a designated location, a gateway opens allowing the contents inside to smoothly flow out. The user can gently squeeze the package to help transfer all of the contents out, and/or apply light suction for liquids that are being taken by mouth. Pluralities of geometric configurations are possible, e.g., a gentle slope where the device glides into the user's mouth with an opening on the end where the product flows out can be constructed. The user's lips provide a perfect seal to ensure that all contents are directly and easily transferred without spillage or waste of product. No caps or secondary pieces that could cause a choking hazard are required for this apparatus. Also, in a preferred embodiment, once the gateway is opened, it is designed to not close again for regulatory purposes.

An embodiment of the invention is directed toward a pre-filled disposable apparatus for delivering a single unit dose of a fluid. The apparatus includes a container capable of holding the pharmacological agent. The container includes a nozzle and an integral valve coupled to the container. The valve is configured to be activated with rotation of the nozzle.

The container may be constructed from a variety of materials, such as, a plastic material, e.g., thermoplastic, selected from a group consisting of polycarbonate, polyethylene, polyester, polystyrene, polypropylene, polysulfone, polyurethane and ethylene-vinyl-acetate. The tube may be bonded and sealed to a hard plastic nozzle.

The nozzle also may be constructed from a variety of materials, such as, a plastic material, e.g., thermoplastic, selected from a group consisting of polycarbonate, polyethylene, polyester, polystyrene, polypropylene, polysulfone, polyurethane and ethylene-vinyl-acetate. The container and the nozzle may be constructed of the same or different materials.

The fluid may be in the form of lotions, creams, ointments, emulsions, solutions, suspensions, combinations thereof and the like. The fluid could also be an alcoholic drink. In a preferred embodiment, the fluid contains a pharmacological agent or medicant, such as, a liquid medications that are only needed for a single use (or unit-dose), e.g., liquid acetaminophen (Tylenol), liquid ibuprofen (Advil), liquid antacid (Maalox), liquid cough and cold medicines, and many others.

The materials for the valve, nozzle or other aspects of the device may be configured to provide a seal, e.g., the material surrounding flexible fluid container may be configured to have a high moisture vapor properties close to or equal to that of high density polyethylene (HDPE). The seal is configured to allow for an extended shelf life, e.g., 1 year or more and more preferably 2 years or more. In one preferred embodiment, the seal is configured as a hermetic seal.

In one embodiment, the apparatus is a two part product that is injection molded. Part one includes a nozzle molded of hard plastic and part two includes a fluid container of a flexible material the container is over molded onto the nozzle.

In a preferred embodiment, the disposal container includes a soft and flexible plastic container to contain a fluid. A hard plastic nozzle is bonded and sealed to a hard plastic nozzle. Fluid is filled into the variable length tube at an open end and then sealed by conventional fill and seal equipment. The fluid is released by rotating the nozzle to release the fluid from the containment area through a fluid channel into the mouth or other container, etc.

The invention is also directed to a method for administering an agent via use of the above referenced device, notably including embodiments where only a single hand need be employed to present the device to a user's lips and without requiring the removal of any caps, tabs, etc. to achieve administration of a desired medication.

According to a further aspect of the present invention, the device may be provided with one or more radiographic markers at the proximal and/or distal ends.

In another embodiment for the delivery device, the major components (cap, neck, tube) are connected by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably attach components of the delivery device: U.S. Patent Appl. No. 2009/0124980 to Chen.

In another embodiment for the delivery device, the major components (cap, neck, tube) are detachable by way of a pedicle dart by threadable rotation to achieve attachment, detachment, and axial movement. Other ways include a quick key engagement, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably engage components: U.S. Patent Appl. No. 2009/0187194 to Hamada.

In another alternative embodiment example, one or more of surfaces of the device are roughened to facilitate use, for example, by the elderly or the blind. The surfaces are provided with Braille markings.

In yet other embodiments, the delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art.

Still another embodiment provides a rifling structure in or on the cap so as to engage the neck portion with a rotational movement. The rifling structure may also be employed within the tube structure, therein delivering a substantially steady pressure and/or rate of delivery of the fluid as a user imparts pressure to the device. The rifling or screw-like movement may also translate to a predetermined delivery of material per full rotation, e.g. each 360 degree rotation equates to about 1 mL of fluid delivered to the user.

Another aspect of the present invention includes providing a device that is disposable. The device may also be at least portions of biocompatible material.

In another embodiment of the present disclosure, the device may be curved longitudinally, or designed to allow stacking with other identical devices or different size devices. One having skill in the art will appreciate that the delivery device may have multiple angles and curved aspects which enable aspects of embodiments of the present disclosure or aid in ergonomics.

In one embodiment of the present disclosure, the device further includes a footing or shelf at the distal end of the device that is nearest the fluid emission site so as to allow precise positioning of the device to a user, for example to inject fluid to a specific site in a user's mouth such as when delivering Novocain to a dental patient.

In certain embodiments, the distal tip region of the device comprises a softer, maliable and/or less rigid material than the remainder of the device. For example, the distal tip could be made of a bioactive collagen.

One skilled in the art will appreciate that the distal end of the device need not be limited to those specific embodiments described above. Other forms, shapes or designs that enable the foregoing aspects of the present invention are hereby incorporated into this disclosure.

One embodiment of the tube provides that the tube is telescoping, thereby allowing its length to be adapted to the particular desires of the user and/or party filling the device with fluid.

In one embodiment of the invention, a fluid delivery device includes a tube portion configured to receive fluid, the tube portion having a first end and a second end, the tube portion also having a tube interior configured to contain a fluid; a neck portion, the neck portion having a first end and a second end, the second end of said neck portion adapted for inserting into the first end of said tube portion; a cap portion, the cap portion having a first end and a second end, the second end of said cap portion adapted for inserting into the first end of said neck portion, the first end of said cap portion having a fluid discharge opening; and a seal portion, the seal adapted to engage between said first end of said neck portion and the second end of said cap portion, wherein the cap portion is configured to rotate relative to the neck portion such that a fluid discharge channel is created from the tube interior to the cap fluid discharge opening.

In another embodiment of the invention, a fluid delivery device includes a tube portion configured to receive fluid, the tube portion having a first end, a second end, and an internal fracture tab mechanism, the tube portion having a tube interior configured to contain the fluid, the first end of the tube portion having a fluid discharge opening, wherein the fracture tab mechanism is configured to rotate within the interior of the tube portion such that a fluid discharge channel is created from the tube interior to the tube first end.

In another embodiment of the invention, a fluid delivery device includes a tube portion configured to receive fluid, the tube portion having a first end and a second end, the tube portion also having a tube interior configured to contain a fluid; a neck portion, the neck portion having a first end and a second end, the second end of neck portion adapted for inserting into the first end of said tube portion; a cap portion, the cap portion having a first end and a second end, the second end of said cap portion adapted for inserting into the first end of said neck portion, the first end of said cap portion having a fluid discharge opening; and a seal portion, the seal adapted to engage between said first end of said neck portion and the second end of said cap portion, wherein the cap portion is configured to traverse relative to the neck portion such that a fluid discharge channel is created from the tube interior to the cap fluid discharge opening.

In yet another embodiment, a disposable apparatus for delivering a predetermined volume of a fluid includes a tube portion sized to fit in a person's hand and having a width dimension, said tube portion configured to hold a predetermined volume of fluid in a range from about 0.5 ounces to about 10 ounces. A cap portion including at least one fluid discharge opening having predetermined aperture dimension that is less than the width dimension of said tube portion is operatively connected to the tube portion.

The cap portion is configured to selectively and reversibly rotate relative to said tube portion between at least 5 degrees and no more than 180 degrees. The cap portion is configured to have a closed position and an open position. The open position is achieved when the cap portion is rotated between at least 5 degrees and no more than 180 degrees. In a closed position, fluid is prevented from being conveyed through said fluid discharge opening when said cap portion.

In a preferred embodiment, a portion of the tube portion is collapsible by exertion of pressure provided by a person's hand to convey the fluid residing in the tube portion through a fluid discharge opening formed in said cap portion when said cap portion is in the open position. Moreover, the cap portion may include a material that provides properties to allow that the cap portion be harder than the tube portion, the cap portion may include a material that provides properties that allow that cap portion to have the same hardness of the tube portion, and the tube portion may include a material that provide properties that allow that tube portion to be harder than the cap portion. In still yet another embodiment, an aspect of the invention is directed towards an improved method for administration of a predetermined amount of fluid. The method includes providing an apparatus according to any embodiment of the invention to a desired treatment situs. Positing the cap portion to the treatment situs and activating the apparatus to permit discharge of the fluid to the treatment situs.

In another embodiment, an aspect of the invention is directed towards a disposable apparatus for delivering a predetermined volume of a fluid including a tube portion configured to hold a predetermined volume of fluid. The apparatus also includes a a cap portion operatively coupled to a tube portion and the cap portion includes at least one fluid discharge opening. The cap portion is configured to rotate relative to said tube portion between an open position and a closed position such that a fluid discharge channel is opened upon rotation of said cap portion to said open position and when the cap portion is rotated to said closed position, the fluid is prevented from exiting said fluid discharge opening by closing the fluid discharge channel.

In still yet another embodiment, a disposable apparatus for delivering a predetermined volume of a fluid includes a tube portion configured to hold the predetermined volume of fluid and a cap portion coupled to the tube portion. The cap portion and tube portion include an integral valve configured to be activated with manual pressure of a thumb or finger on an external surface of the tube portion. In this embodiment, the cap portion and the tube portion may be one single piece, that is, the entire apparatus would be a tube portion.

In another embodiment, the apparatus includes a container including at least one fluid discharge port, an internal portion and an external surface. An integral valve on an internal portion of the container is operatively configured to allow fluid communication to the at least one discharge port upon activation. The integral valve is configured to be activated with manual pressure of a thumb or finger to an external surface of the container and upon activation fluid communication between the at least one discharge port and the internal portion of the container is possible.

One of ordinary skill in the art will appreciate that embodiments of the present disclosure may have various sizes.

One or ordinary skill in the art will appreciate that embodiments of the present disclosure may be constructed of materials known to provide, or predictably manufactured to provide the various aspects of the present disclosure. These materials may also include, for example, PEEK, carbon fiber, ABS plastic, polyurethane, rubber, latex, synthetic rubber, and other fiber-encased resinous materials, synthetic materials, polymers, and natural materials. In another embodiment, some or all elements of the device, or portions of some or all of the elements, are luminescent. Also, in another embodiment, some or all elements of the device, or portions of some or all of the elements, include lighting elements.

In one embodiment of the invention, comprising the device configured with twist opening feature, hinged fracture tab opening feature, and slider opening feature, the device may be filled and sealed from either end of the device; for example, from the second end of the device with a hot air seal, thermal compression seal, crimping means, or other means known by one skilled in the art or, for example, from the first end of the device via the fluid discharge opening.

In one embodiment of the invention, comprising the device configured with twist opening feature, hinged fracture tab opening feature, and slider opening feature, the device may be configured such that its fluid contents have an extended shelf life; extended shelf life may be defined comprising one year, two years, three years, four years and five years.

In one embodiment of the invention, comprising the device configured with twist opening feature, hinged fracture tab opening feature, and slider opening feature, the device may be made of materials know to one skilled in the art to be preferable and/or useful for the applications disclosed, to include but not limited to delivery of medicine, gels, lotions and drinking alcohol.

In one embodiment of the invention, comprising the device configured with twist opening feature, hinged fracture tab opening feature, and slider opening feature, the device may be configured with ergonomic features for fluid delivery to the mouth, to include those disclosed above.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 3A is a cross-sectional side view of the device in the open position;

FIG. 3B is a front view of the device in the open position;

FIG. 3C is a close up cross-sectional side view of the device in the open position;

FIG. 7A is a side view of the device with hinged opening feature;

FIG. 7B is a front view of the device with hinged opening feature;

FIG. 7C is a side view of the front the device with hinged opening feature;

FIG. 7D is a view of front and cross-sectional side view of the device with hinged opening feature;

FIG. 7E is a cross-sectional side view of the device with hinged opening feature;

FIG. 8A is a top view of the device with hinged opening feature;

FIG. 8B is a side view of the device with hinged opening feature;

FIG. 8C is a front view of the device with hinged opening feature in the open position;

FIG. 8D is a top view of the device with hinged opening feature;

FIG. 8E is a side view of the device with hinged opening feature;

FIG. 8F is a front view of the device with hinged opening feature in the open position;

FIG. 8G is a top view of the device with hinged opening feature;

FIG. 8H is a side view of the device with hinged opening feature;

FIG. 8I is a front view of the device with hinged opening feature in the open position;

FIG. 15A is a top view of the device with hinged opening feature;

FIG. 15B is a side view of the device with hinged opening feature in the open position;

FIG. 15C is a front view of the device;

FIG. 15D is a perspective view of the device in the open position with hinged opening feature;

DETAILED DESCRIPTION

Reference will now be made in detail to embodiments of the present invention, examples of which are illustrated in the accompanying drawings.

Figure 1A:
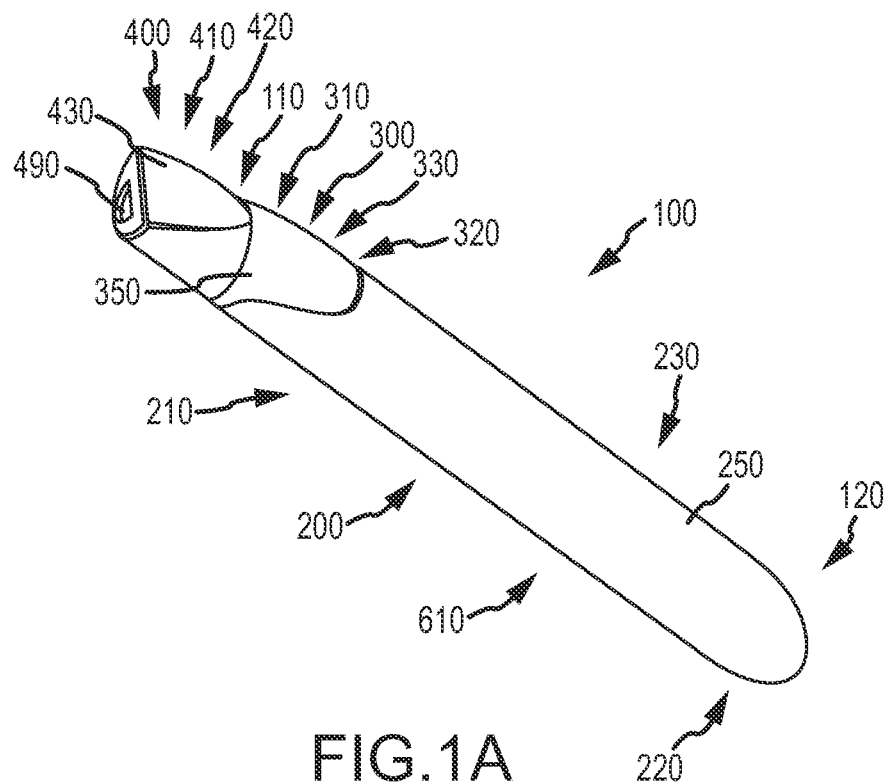
FIG. 1A is a perspective view of the device with twist opening feature and in the open configuration.

In regard to FIG. 1A a perspective view of the device is provided. In this embodiment of the invention the device 100 is generally configured in a cylinder tube configuration with a twist opening feature. The device 100 generally has a device first end 110 and a device second end 120. Further, the device includes a tube 200, a neck 300, and a cap 400.

The tube section 200 includes a tube first end 210, a tube second end 220, a tube upper end 230, and tube lower end (not shown). In addition, the tube 200 includes a tube exterior surface 250, tube interior surface (not shown), and tube thickness.

The neck portion of the device 100 includes a neck 300. The neck 300 includes a neck first end 310, a neck second end 320, a neck upper end 330, neck lower end (not shown), neck exterior surface 350. The cap section 400 of the device 100 includes a cap first end 410, a cap second end 420, a cap exterior surface 430, and a cap second exterior surface 440. Furthermore, the cap 400 includes a cap fluid discharge opening 490. FIG. 1A depicts the device 100 in the closed configuration that is unable to discharge its contents.

Figure 1B:
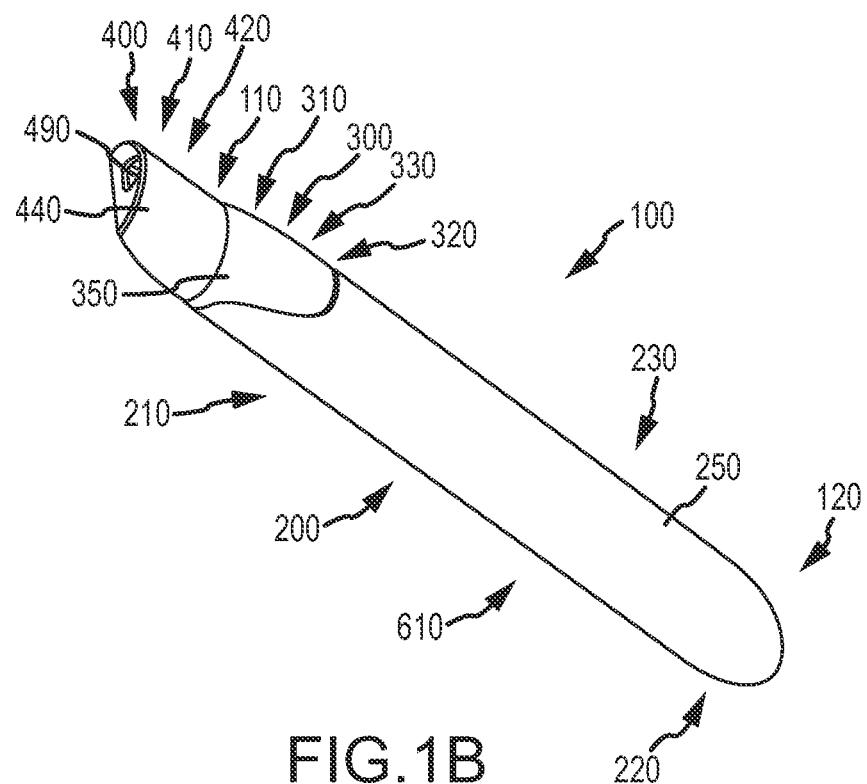
FIG. 1B is a perspective view of the device with twist opening feature and in the closed configuration.

Referring now to FIG. 1B, a perspective view of the device 100 is presented. FIG. 1B is similar to FIG. 1A except the cap 400 section of the device 100 has been rotated into its open position, allowing fluid or the contents of the device 100 to be discharged. The device 100 generally has a device first end 110 and a device second end 120. Further, the device includes a tube 200, a neck 300, and a cap 400.

The tube section 200 includes a tube first end 210, a tube second end 220, a tube upper end 230, and a tube lower end (not shown). In addition, the tube 200 includes a tube exterior surface 250, tube interior surface (not shown), and tube thickness.

The neck portion of the device 100 includes a neck 300, including a neck first end 310, a neck second end 320, a neck upper end 330, and a neck lower end (not shown). The cap section 400 of the device 100 comprises a cap first end 410, a cap second end 420, a cap exterior surface 430, and a cap second exterior surface 440. Furthermore, the cap 400 includes a cap fluid discharge opening 490. FIG. 1B depicts the device 100 in the open configuration that is able to discharge its contents.

Figure 2A:
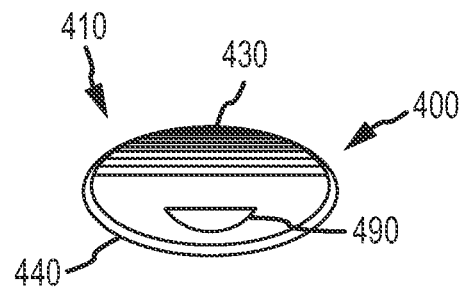
FIG. 2A is a front view of the device with twist opening feature in the closed position.
Figure 2B:
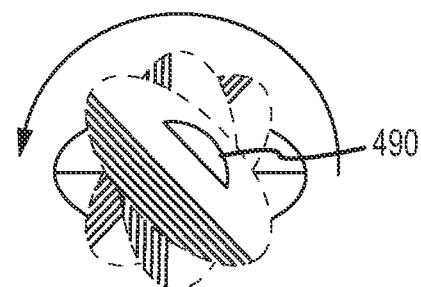
FIG. 2B is a rotational front view of a cross-section of the device with twist opening feature.
Figure 2C:
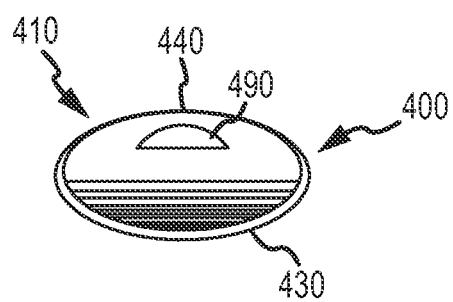
FIG. 2C is a front and cross-sectional side view of the device with twist opening feature in the open position.

Referring now to FIGS. 2A-2C, an end view of the device 100 is presented showing the rotation of the cap 400 from its closed position shown in FIG. 2A through an intermediary position shown in FIG. 2B to an open position shown as FIG. 2C. Specifically, FIG. 2A presents an end view of the cap 400 of the device 100, showing the cap 400 features of a cap first end 410, a cap second end 420, a cap first exterior surface 430, a cap second exterior surface 440, and a cap fluid discharge opening 490.

In FIG. 2C, the device 100 is shown in the open configuration. The cap 400 includes cap first end 410, cap first exterior surface 430, cap second exterior surface 440, and cap fluid discharge opening 490. FIGS. 2A-C illustrates the cap opening in a counter clockwise manner shown in its interim rotation state as FIG. 3B.

Figure 3D:
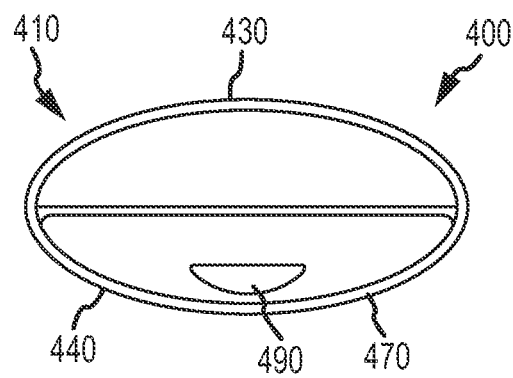
FIG. 3D is a front view of the device in the closed position.

Referring now in detail FIGS. 3A-F, various ends and cross-sectional side views of the device in the cylinder tube configuration with twist opening feature are presented. FIG. 3A presents the device 100 featuring a tube 200, device first end 110, and device second end 120. Further, FIG. 3A illustrates the neck portion 300, a neck thickness 370, and a cap fluid discharge opening 490. A broken seal 530 is also shown in this open configuration.

FIG. 3B illustrates an end view of FIG. 3A and FIG. 3C presents a close up cross sectional end view of FIG. 3A.

In FIG. 3B the cap 400 is shown with a cap first end 410, cap first exterior surface 430, a cap second exterior surface 440, cap thickness 470, and cap fluid discharge opening 490.

FIG. 3C presents a close up cross-sectional view of FIG. 3A depicting the neck 300 and features of the cap 400.

Referring to FIG. 3C, the neck 300 is shown with a neck thickness 370, and the cap 400 is shown with cap first exterior surface 430, and cap fluid discharge opening 490 illustrated. FIGS. 3A-C presents the device 100 in the open configuration allowing fluid or substance to be emitted along path 600 (the fluid discharge channel) out from the device 100 through cap fluid discharge opening 490. Further, FIG. 3C illustrates a seal component 500 and seal second thickness 520 in the configuration of the FIGS. 3A-C. The device has been rotated according to FIGS. 2A-C to move to the open discharge configuration.

Figure 3E:
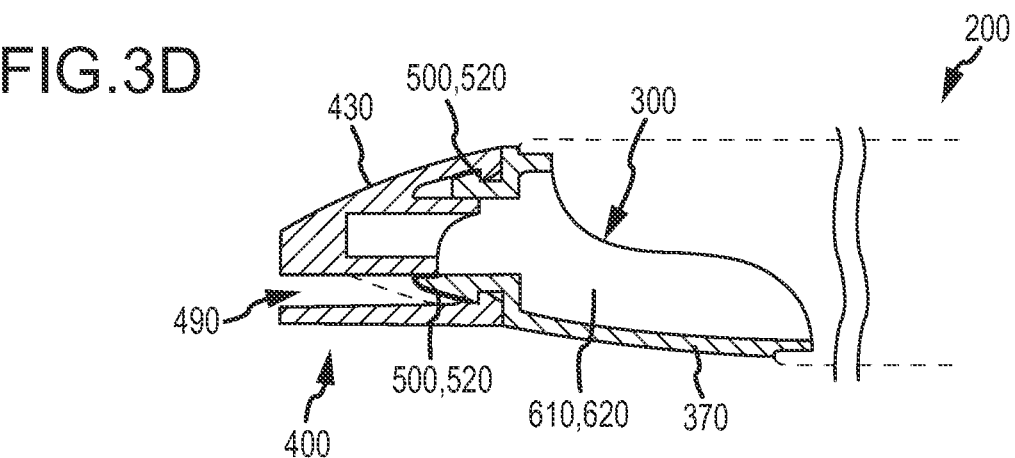
FIG. 3E is a close up cross-sectional side view of the device in the closed position.

FIGS. 3D-E presents the device 100 in the closed configuration, which does not allow fluid contents 620 to be discharged from the device 100. FIG. 3D presents an end view of the device 100 focusing on the cap 400 elements, shown in FIG. 3 are the cap 400, the cap first end 410, the cap first exterior surface 430, the cap second exterior surface 440, the cap thickness 470, and cap fluid discharge opening 490.

FIG. 3E presents a cross-sectional view of FIG. 3D of the device 100 as figured in its closed configuration and includes the tube 200, neck 300 and cap 400. FIG. 3E depicts cap fluid discharge opening 490, cap first exterior opening 430, neck thickness 370, seal 500, and seal second thickness 520.

Figure 3F:
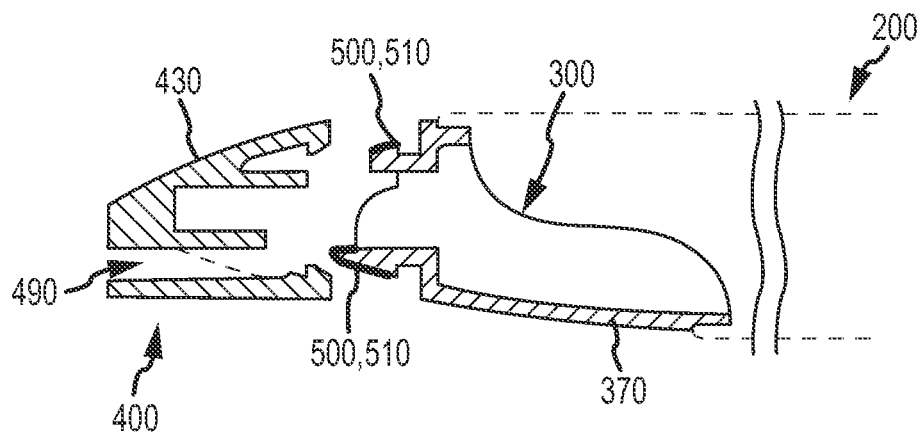
FIG. 3F is a close up cross-sectional view of the device disassembled.

FIG. 3F presents the device 100 in its closed configuration similar to FIG. 3E except with the cap structure 400 disassembled from the tube portion 200 and neck section 300. FIG. 3F presents features of neck thickness 370, cap first exterior surface 430, and cap fluid discharge opening 490. Also depicted in FIG. 3F are seal first thickness 510 and seal second thickness 520. Upon engagement between the cap 400 and neck 300, the seal initially with seal first thickness 510, typically reduces to seal second thickness 520.

Figure 4A:
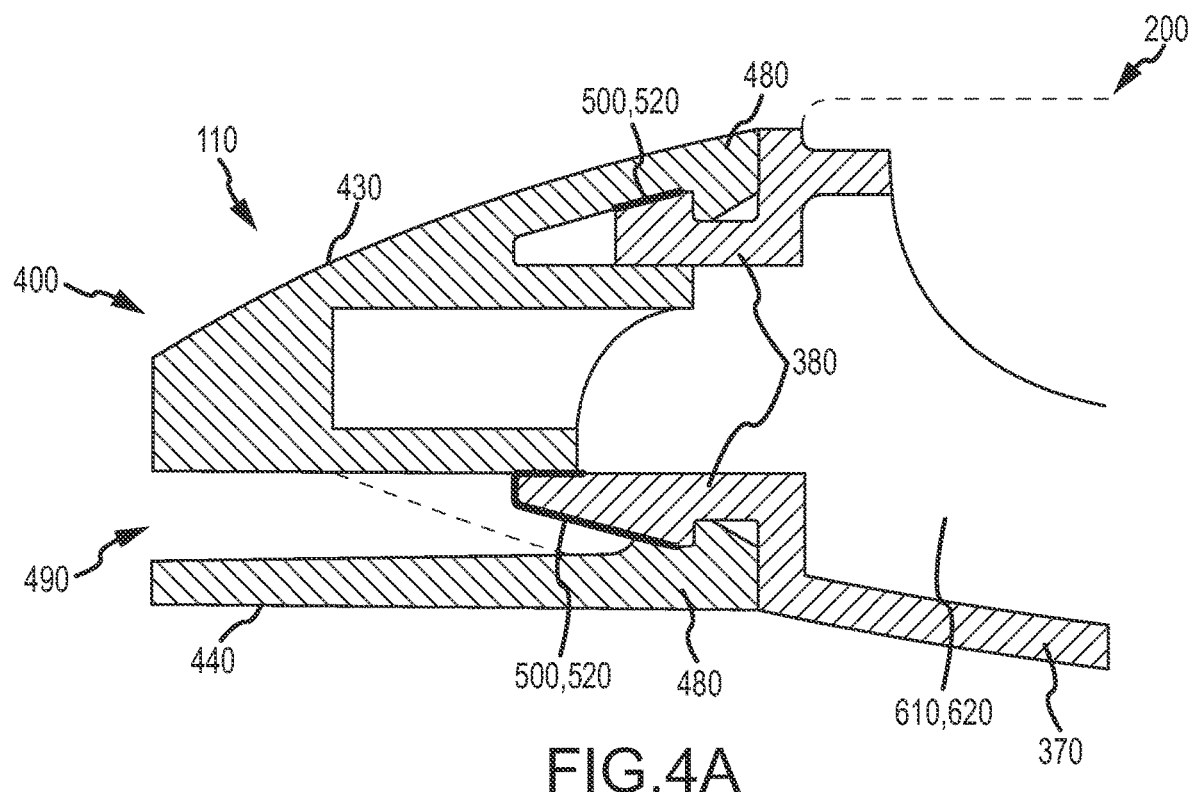
FIG. 4A is a close up cross-sectional side view of the device in the closed position.
Figure 4B:
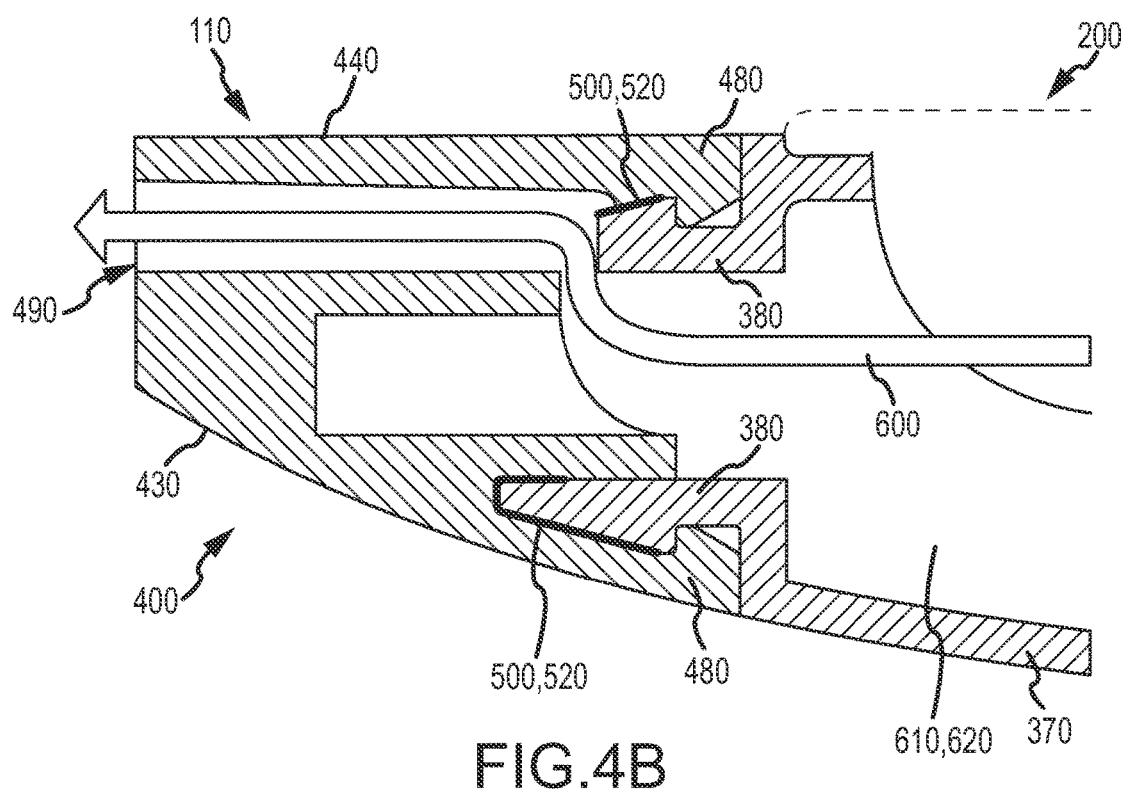
FIG. 4B is a close up cross-sectional side view of the device in the open position

FIGS. 4A-B presents additional close up cross-sectional views of the device first end 110. FIG. 4A presents the device 100 in the closed configuration, while FIG. 4B presents the device 100 in the open configuration.

Turning now to FIG. 4A, the device 100 includes the tube 200, neck thickness 370, neck cap inner connection structure 380, cap-neck interconnect structure 480, cap 400, cap first exterior surface 430, cap second exterior surface 440, and cap fluid discharge opening 490. FIG. 4A also presents seal 500 and seal second thickness 520. FIG. 4A presents the device 100 in the open configuration in which fluid contents 620 may be emitted through the device cap 400 at the cap fluid discharge opening 490. The fluid contents 620 are emitted along path fluid discharge channel 600.

Turning now to FIG. 4B, the device first end 110 is shown with elements tube 200, neck thickness 370, neck cap inner connection structure 380, cap 400, cap first exterior surface 430, cap second exterior surface 440, and cap fluid discharge opening 490 are shown. The device 100 is in the open configuration in which fluid contents 620 may be emitted through the device cap 400 at the cap fluid discharge opening 490. The fluid contents 620 are emitted along path fluid discharge channel 600.

Figure 5A:
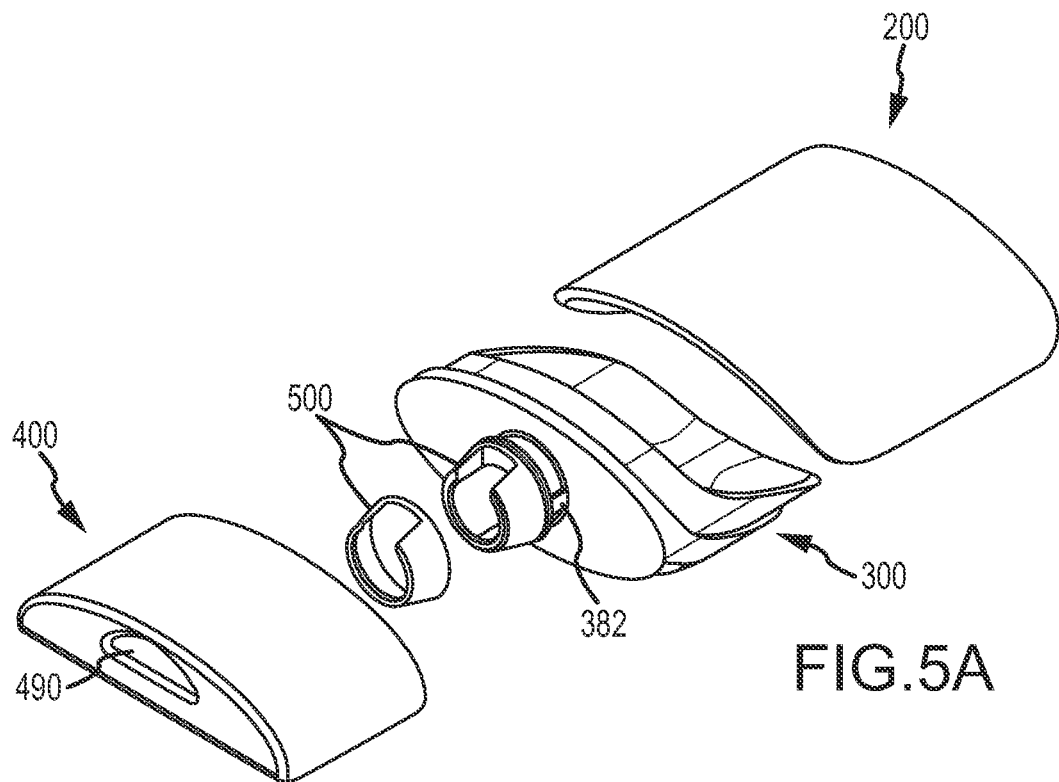
FIG. 5A is a cut-away view of the device with twist opening feature in the open configuration.
Figure 5B:
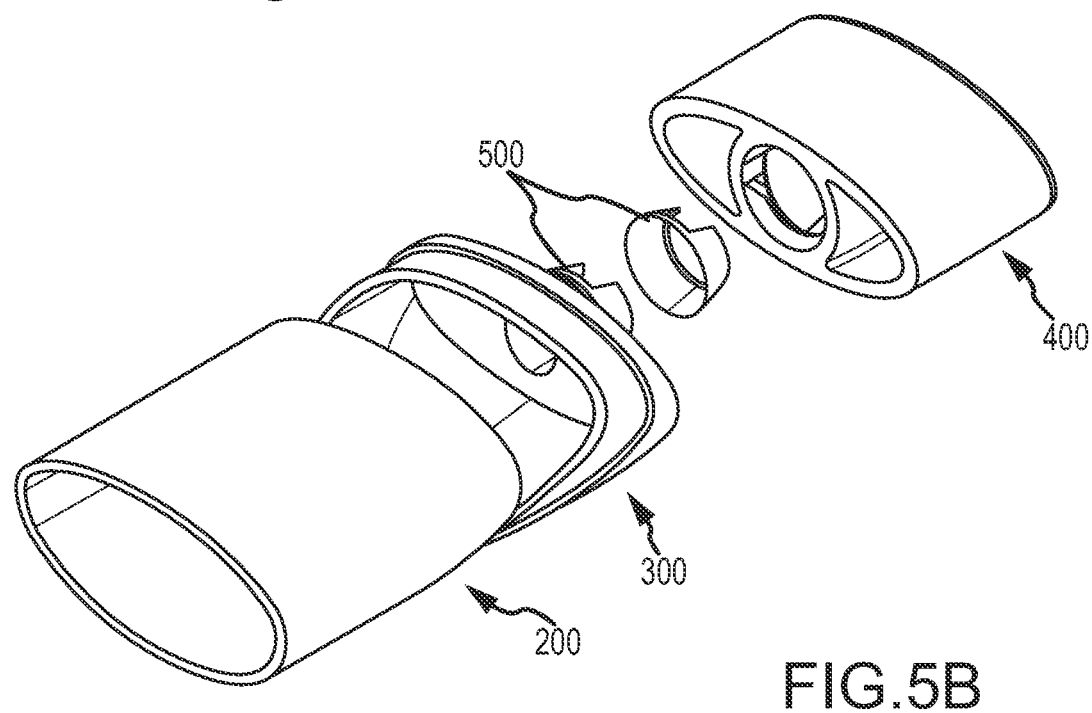
FIG. 5B is another cut-away view of the device with twist opening feature in the open configuration.

FIGS. 5A-B presents a disassembled view of the device 100 with particular focus on the seal 500 element. FIG. 5B is a reverse view of FIG. 5A. Both FIGS. 5A and 5B depict the device in the open configuration in which fluid content 620 may be emitted through cap fluid discharge opening 490. In FIG. 5A the device 100 is shown with a tube 200, neck 300, cap 400, and seal 500. In addition, neck alignment ridge 382 in identified. FIG. 5B, is a reverse view of FIG. 5A, and presents the device 100 with tube 200, neck 300, cap 400, and seal 500. FIG. 5B also identifies the cap alignment grove 484. Both FIGS. 5A and 5B present an additional view of the seal 500 for additional detail. Only one seal 500 is present in the device in this embodiment of the device 100. Neck alignment ridge 382 engages cap alignment grove 484 to secure a connection between the cap 400 component and the neck component 300.

FIGS. 6A-D provides additional views of the embodiment of the device 100 in a cylinder tube configuration with a twist opening feature.

Figure 6A:
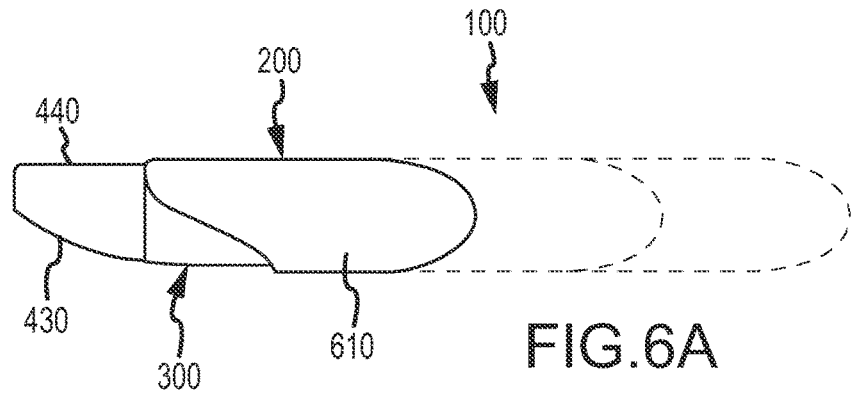
FIG. 6A is a side view of the device with twist opening feature in the open configuration.
Figure 6B:
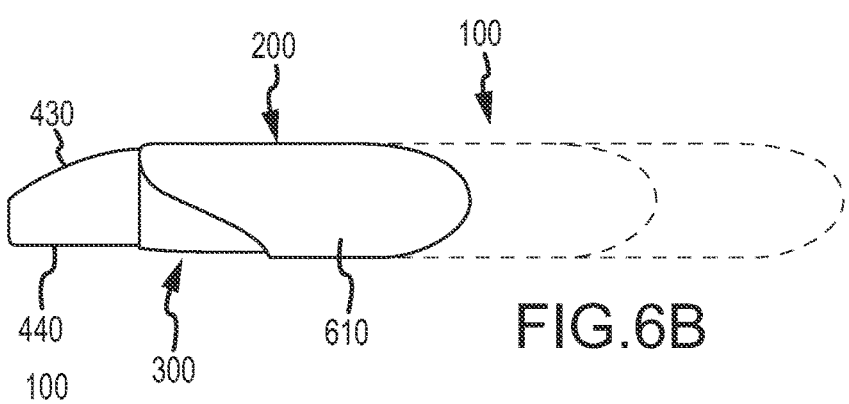
FIG. 6B is a side view of the device with twist opening feature in the closed configuration.

FIGS. 6A-6B illustrate side views of the device 100 in an open configuration and a closed configuration, respectably. FIG. 6A presents the device 100 with tube 200, neck 300, cap first exterior surface 430, cap second exterior surface 440, and fluid containment area 610. FIG. 6B presents the device 100 in its closed configuration with tube 200, neck 300, cap first exterior surface 430, cap second exterior surface 440 as well as fluid containment area 610. The dashed lines in FIGS. 6A and 6B depict extensions of the device 100 to allow additional fluid containment area 610. In each of the dashed line configurations of FIGS. 6A and 6B specific volumes of fluid contents 620 would be featured, e.g., 5 mL, 10 mL, and 15 mL. The size of the device and its ability to contain varying degrees of fluid content 620 are enabled by extension of the tube portion 200.

Figure 6C:
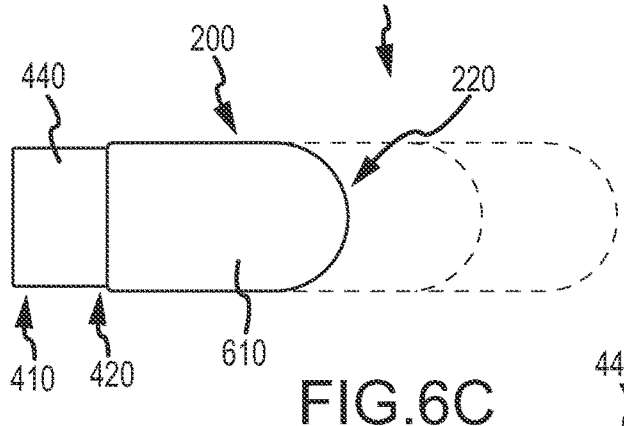
FIG. 6C is a top view of the device.
Figure 6D:
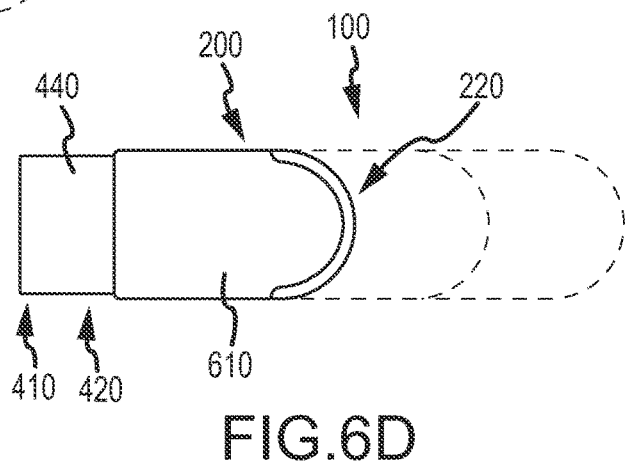
FIG. 6D is a top view of the device with end-filling feature at the tube second end.

FIGS. 6C and 6D depicts the device 100 in a top view showing the tube portion 200, a tube second end 220, cap first end 410, cap second end 420, and cap second exterior surface 420. Similar to FIGS. 6A and 6B, FIGS. 6C and 6D depict the device with varying degrees of elongation of the tube section 200 to allow for varying levels of fluid containment area 610 and therefore varying amounts of fluid content 620 volume. FIG. 6D includes a tube second end location 220 that enables fluid content 620 filling of fluid containment area 610. More specifically, the second end location 220 is used to fill the tube 200 to the desired volume and then sealed in a thermal compression manner as known in the art.

FIGS. 7-15 depicts the device in the cylinder tube configuration with a hinged fracture tab opening feature.

FIG. 7A presents device 100 with tube 200, cap first exterior surface 430, cap second exterior surface 440, and fracture tab 700 with fracture tab pressing point 710 and fracture tab position one 712.

FIG. 7B is a front view of FIG. 7A presenting the cap fluid discharge opening 490, cap second exterior surface 440, cap first exterior surface 430, and cap thickness 470.

FIG. 7C presents a close up cross-sectional view of the device 100 as depicted in FIG. 7C. FIG. 7C presents the tube 200, cap first exterior surface 430, cap second exterior surface 440, fracture tab 700 with fracture tab position one 712 and fracture tab position two 714. When a user depresses by applying a downward vertical force at fracture tab pressing point 720 fracture tab 700 depresses thereby allowing fluid to discharge from device 100.

FIGS. 7D-7E presents additional views of the device 100. FIG. 7D is a cross-sectional front end view of the device at section A-A of FIG. 7E. FIG. 7E depicts the fracture tab 700 in both its fracture tab positions one 712 position and its fracture tab position two 714 configuration. When the fracture tab 700 is in its fracture tab position one 712 position, fluid is unable to discharge from device 100 through cap fluid discharge opening 490. However, when a user engages device 100 by pressing hinge 700 at fracture tab pressing point 710, the hinge 700 rotates downward as shown in FIG. 7E to the position of fracture tab position two 714 thereby allowing fluid to emit through cap fluid discharge opening 490. FIG. 7D depicts cap fluid discharge opening 490, cap second exterior surface 440, and cap first exterior surface 430. In this embodiment, the fracture tab 700 has a radius of curvature to permit easier fracturing and allow the fracture tab 700 to be a location closer to an inner surface of the tube.

Figure 8J:
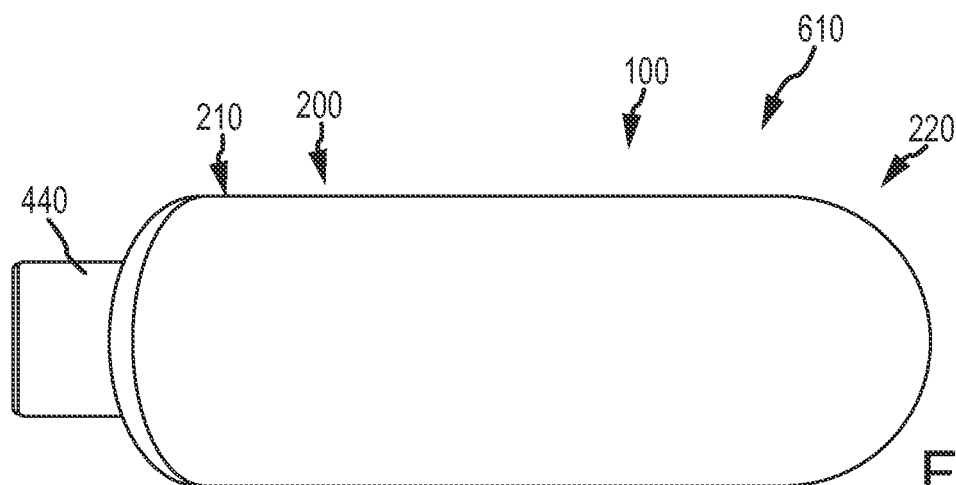
FIG. 8J is a top view of the device with hinged opening feature.

FIGS. 8A-L depicts the device 100 in various configurations; in particular, various configurations of the tube shape and length. FIGS. 8A-C depicts three different views of a configuration of device 100, detailing the tube 200, the tube first end 210, tube second end 220, cap first exterior surface 430, cap second exterior surface 440, and cap fluid discharge opening 490. FIGS. 8A-L are representative of cylinder tube configurations which could feature a twist opening feature and/or a hinge fracture tab opening feature or other embodiments of the opening feature.

FIGS. 8D-F depict another three different views of a configuration of the device 100. The embodiment of FIGS. 8D-F are similar to FIGS. 8A-C, yet would allow a greater amount of fluid content 620 to be stored in fluid containment area 610.

FIGS. 8G-I presents three different views of the device 100. The embodiments shown in FIGS. 8G-I would contain an additional fluid content 620 through those of FIGS. 8D-F and figure FIGS. 8A-C. FIGS. 8G-I depict the device 100 with elements tube 200, tube first end 210, cap second exterior surface 440, cap first exterior surface 430, and cap fluid discharge opening 490.

Figure 8K:
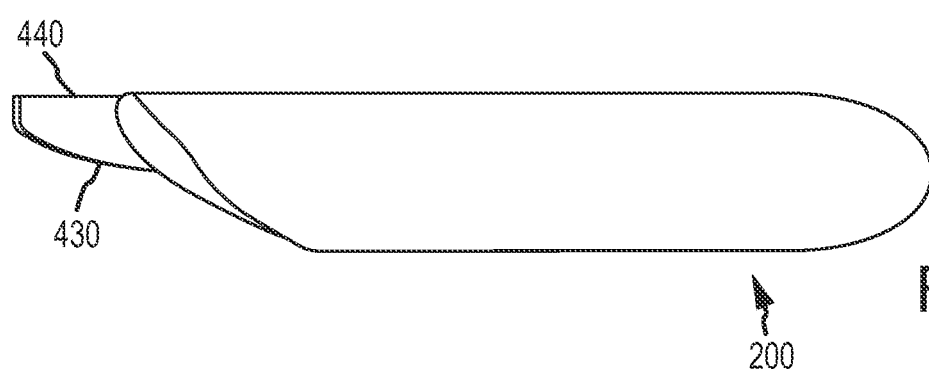
FIG. 8K is a side view of the device with hinged opening feature.
Figure 8L:
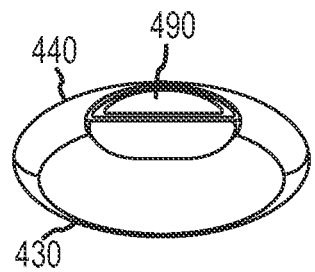
FIG. 8L is a view of front view of the device with hinged opening feature.

FIGS. 8J-L illustrates another embodiment of the invention shown with a particularly large fluid containment area 610. The intended fluid containment area 610 would store at least 50 mL of fluid content 620. FIGS. 8J-L depicts the device 100 with tube 200, tube first end 210, cap first exterior surface 430, cap second exterior surface 440, and cap fluid discharge opening 490.

Figure 9A:
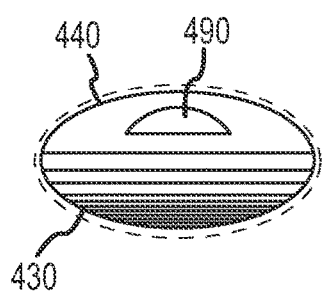
FIG. 9A is a front view of the device with hinged opening feature.
Figure 9B:
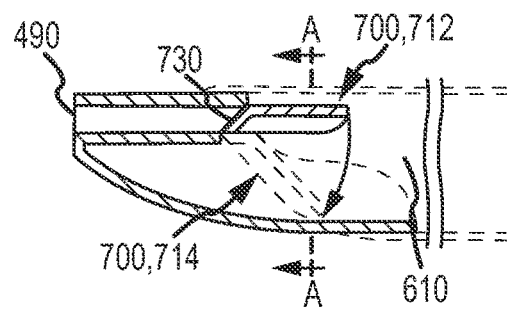
FIG. 9B is a side cross-sectional view of the device with hinged opening feature.
Figure 9C:
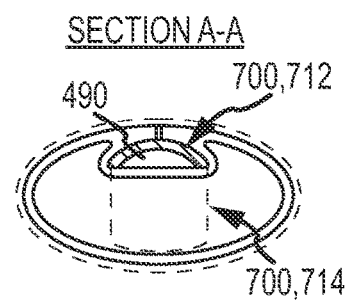
FIG. 9C is a front cross-sectional view of the device with hinged opening feature.

FIGS. 9A-C depicts the device 100 in a cylinder tube configuration with hinged fracture tab opening feature. FIG. 9A is a front view of the device with cap fluid discharge opening 490, cap first exterior surface 430, and cap second exterior surface 440. FIG. 9B is a cross-sectional view of the device 100 depicting the cap fluid discharge opening 490, the fracture tab 400 and details of the fracture tab 700 in both fracture tab position one 712 and fracture tab position two 714. Further, FIG. 9B identifies the front fracture line 730. A user, in pressing the fracture tab 700 downward, would impart a force to the fracture tab position 700 such that the fracture tab 700 rotates between fracture tab position one 712 and fracture tab position two 714. In fracture tab position one 712 no fluid is emitted from cap fluid discharge opening 490. However, in fracture tab position two 714, fluid may be emitted through fluid discharge opening 490. FIG. 9C presents a cross-sectional A-A of FIG. 9B showing the cap fluid discharge opening 490 and the fracture tab 700 in both its fracture tab position one 712 and fracture tab position two 714 configurations.

Figure 10A:
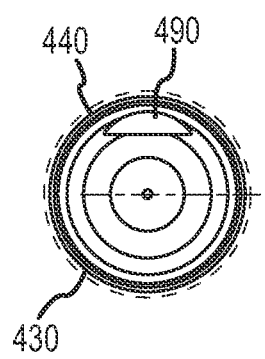
FIG. 10A is a front view of the device with hinged opening feature.
Figure 10B:
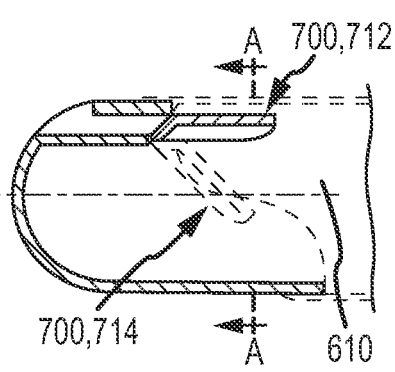
FIG. 10B is a side cross-sectional view of the device with hinged opening feature.
Figure 10C:
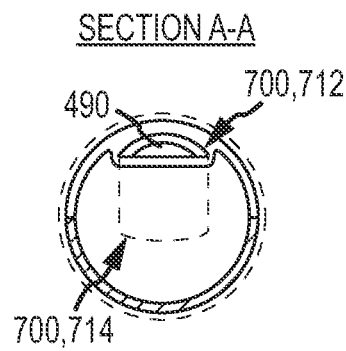
FIG. 10C is a front cross-sectional view of the device with hinged opening feature.

FIGS. 10A-C presents another configuration of the device 100 in a cylinder tube configuration with hinged fracture tab opening feature. FIG. 10A is a front view of the device depicting the cap fluid discharge opening 490, cap second exterior surface 440, and cap first exterior surface 430. FIG. 10B depicts a cross-sectional side view of the device with fracture tab 700 with both the fracture tab position one 712 and fracture tab position two 714 positions. FIG. 10C presents section A-A of 10B showing cap fluid discharge opening 490, and fracture tab 700 with both the fracture tab position one 712 and fracture tab position two 714 configurations.

Figure 11A:
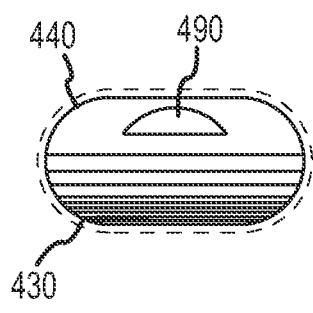
FIG. 11A is a front view of the device with hinged opening feature.
Figure 11B:
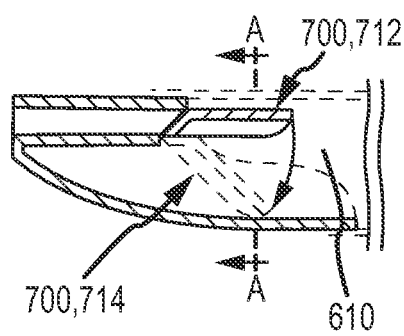
FIG. 11B is a side cross-sectional view of the device with hinged opening feature.
Figure 11C:
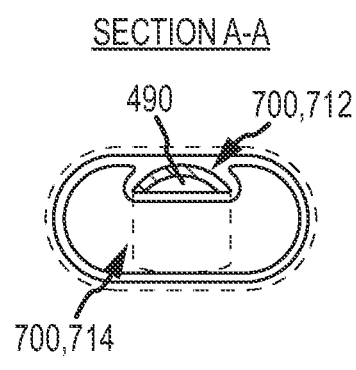
FIG. 11C is a front cross-sectional view of the device with hinged opening feature.

FIGS. 11A-C presents another embodiment of the device 100 in an oblong cylinder tube configuration with hinged fracture tab opening feature. FIG. 7A depicts the front view of the device 100 cap fluid discharge opening 490, cap first exterior surface 430, and cap second exterior surface 440. FIG. 7B presents a cross-sectional side view of the device featuring a fracture tab 700 with both the fracture tab position one 712 and fracture tab position two 714 configurations. FIG. 11C presents a cross-sectional A-A of FIG. 11B showing the cap fluid discharge opening 490 and the fracture tab 700 in both its fracture tab position one 712 and fracture tab position two 714 configurations.

Figure 12A:
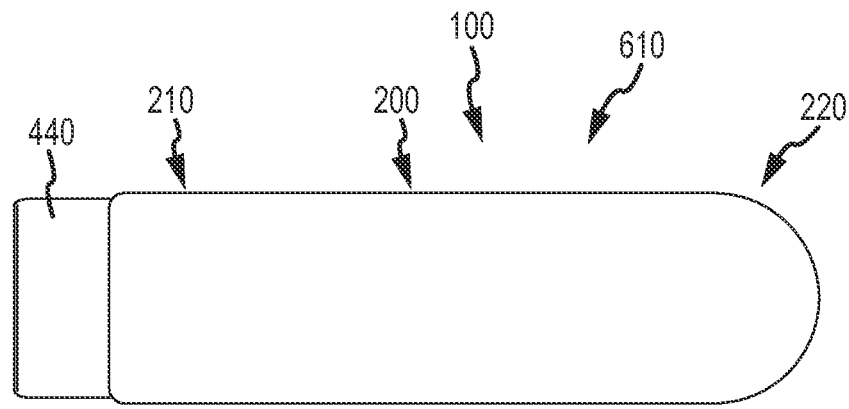
FIG. 12A is a top view of the device with hinged opening feature.
Figures 12B, 12C:
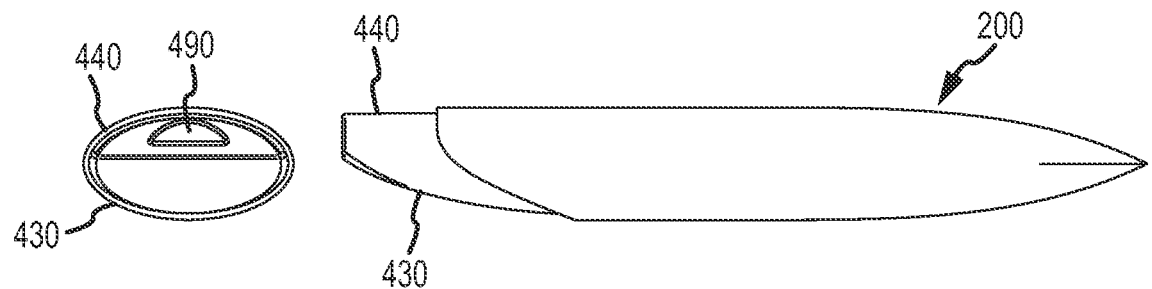
FIG. 12B is a front view of the device with hinged opening feature in the open position.
FIG. 12C is a side view of the device with hinged opening feature with end filling feature at the tube second end.
Figure 12D:
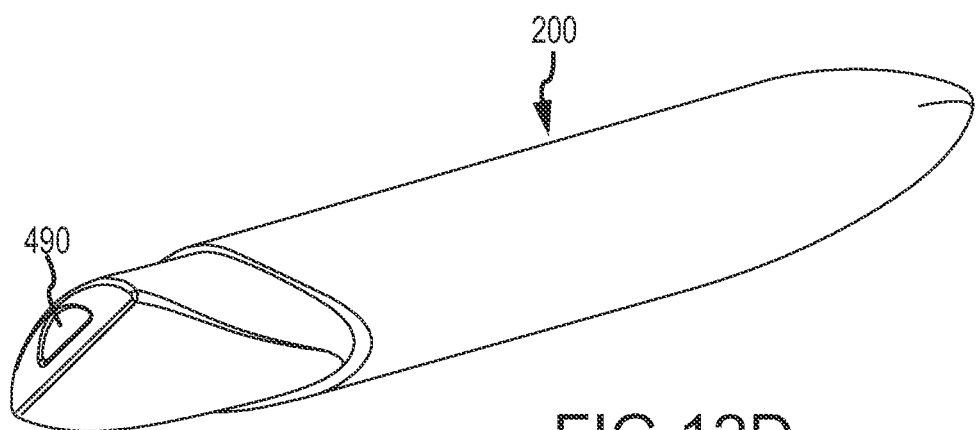
FIG. 12D is a perspective view of the device with hinged opening feature with end filling feature at the tube second end.

FIGS. 12A-D presents the device 100 in yet another embodiment of the cylinder tube configuration. The embodiment of FIGS. 12A and 12D are contemplated for use with both the twist opening feature and hinged fracture tab opening feature and could also be useful in other opening feature configurations. FIGS. 12A-C presents a three view of the device 100 while FIG. 12D presents a perspective view. Shown in FIGS. 12A-D are the device 100, tube 200, tube first end 210, tube second end 220, cap first exterior surface 430, cap second exterior surface 440, and cap fluid discharge opening 490. In this embodiment, the second end 220 is used to file the tube 200 and subsequently sealed via thermal compression or other technique as known in the art.

Figure 13A:
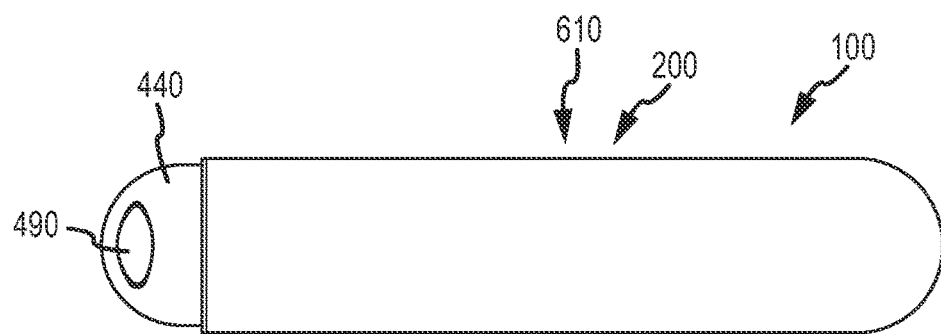
FIG. 13A is a top view of the device with hinged opening feature.
Figures 13B, 13C:
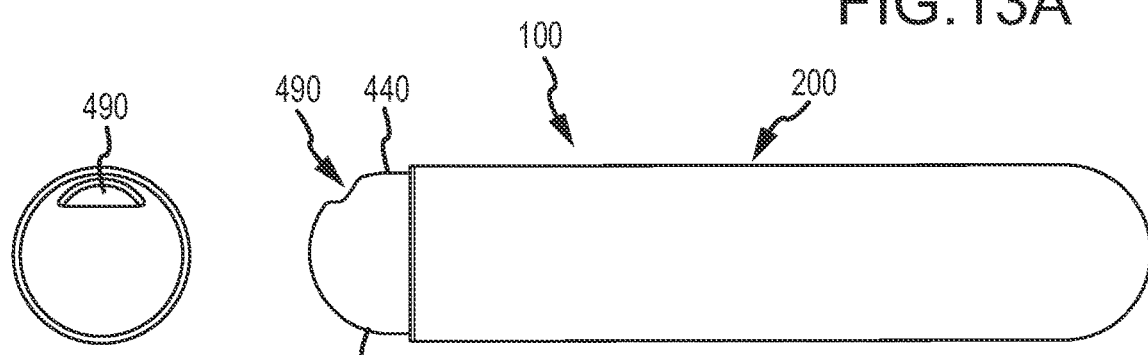
FIG. 13B is a side view of the device with hinged opening feature in the open position.
FIG. 13C is a front view of the device.
Figure 13D:
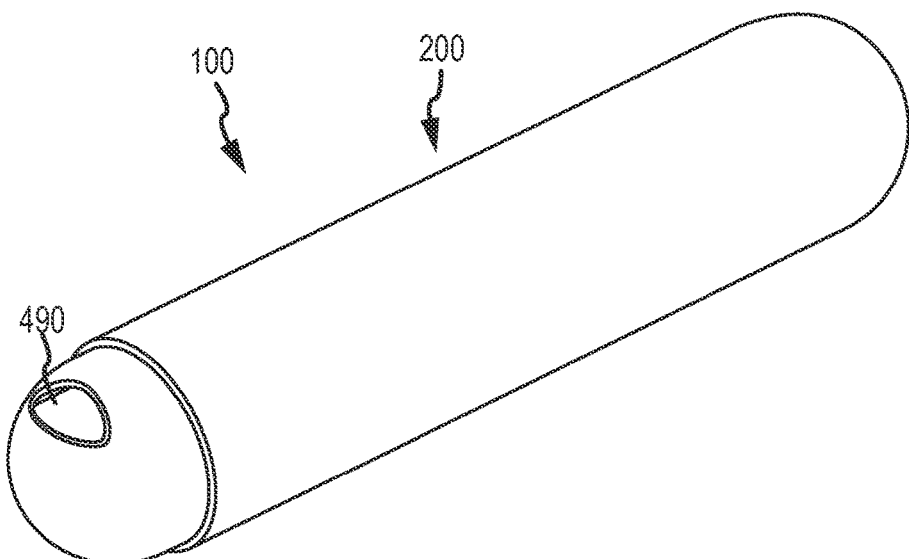
FIG. 13D is a perspective view of the device in the open position with hinged opening feature.

FIGS. 13A-D present yet another embodiment of the invention configured as a generally cylinder or round tube 200. FIGS. 13A-C presents a three view perspective of this embodiment, while FIG. 13D presents a perspective view. Elements shown in FIGS. 13A-D are the device 100, tube 200, cap first exterior surface 430, cap second exterior surface 440, and cap fluid discharge opening 490.

Figure 14A:
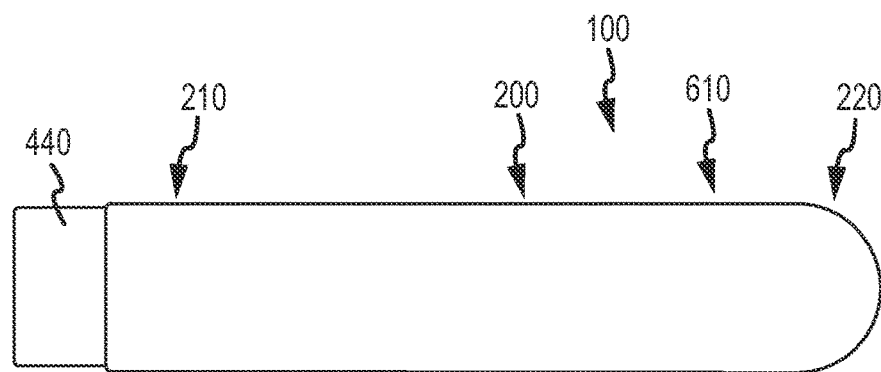
FIG. 14A is a top view of the device with hinged opening feature.
Figures 14B, 14C:
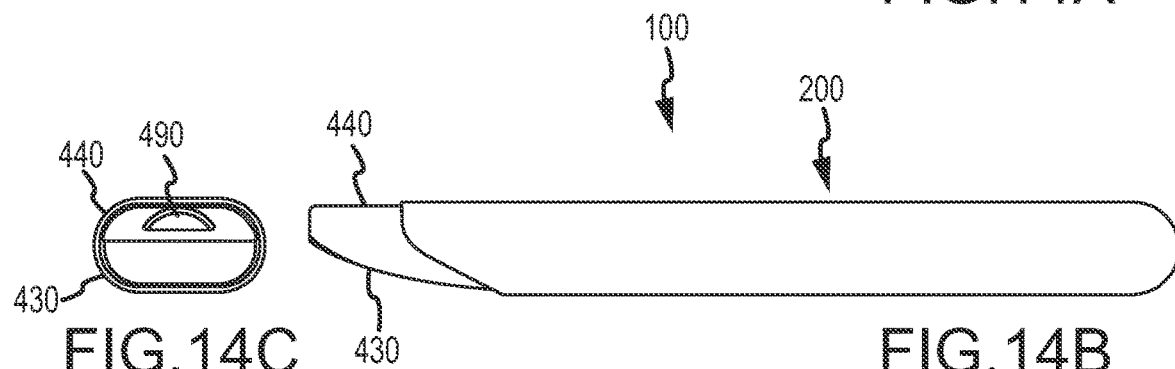
FIG. 14B is a side view of the device with hinged opening feature in the open position.
FIG. 14C is a front view of the device.
Figure 14D:
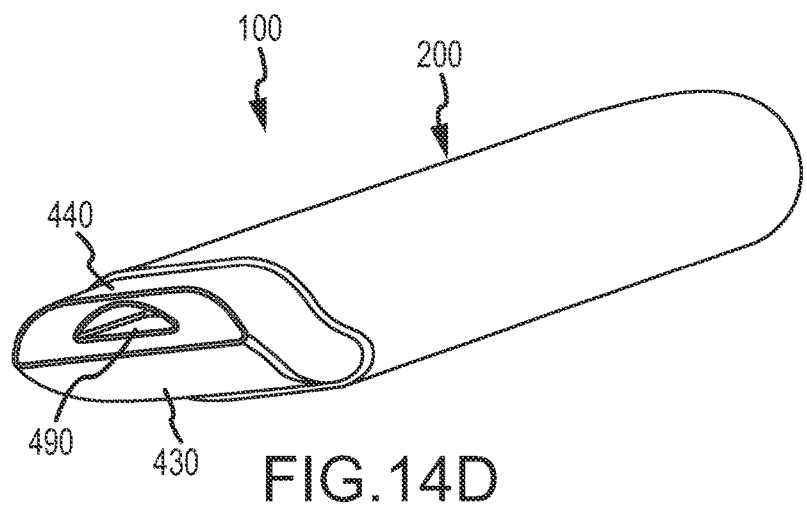
FIG. 14D is a perspective view of the device in the open position with hinged opening feature.

FIGS. 14A-D present yet another embodiment of the invention configured as a generally cylinder or round tube 200. FIGS. 14A-C presents a three view perspective of this embodiment, while FIG. 14D presents a perspective view. Elements shown in FIGS. 14A-D are the device 100, tube 200, cap first exterior surface 430, cap second exterior surface 440, and cap fluid discharge opening 490. This embodiment is dubbed the "racetrack" embodiment.

FIGS. 15A-D present yet another embodiment of the invention configured as a generally cylinder or round tube 200. FIGS. 15A-C presents a three view perspective of this embodiment, while FIG. 15 presents a perspective view. Elements shown in FIGS. 15A-D are the device 100, tube 200, cap first exterior surface 430, cap second exterior surface 440, and cap fluid discharge opening 490.

Figure 16:
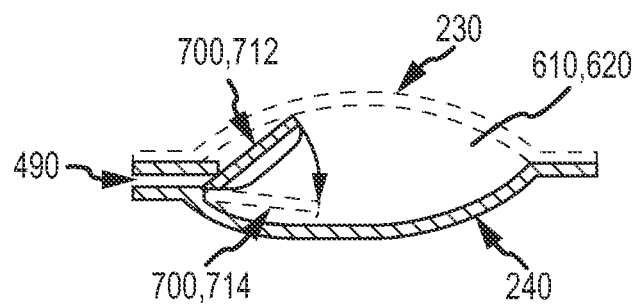
FIG. 16 cross sectional of the device with clamshell/hinged opening feature.

Turning to FIG. 16, a cross-sectional side view of the device 100 is depicted with tube upper end 230, tube lower end 240, cap fluid discharge opening 490, and fracture tab 700 in both its fracture tab position one (or closed position) 712, and fracture tab position two (or open position) 714. When a user presses on the tube upper end 230, so as to engage fracture tab 700, with sufficient pressure to push fracture tab 700 downward, tab 700 rotates in the direction as depicted by the arrow in FIG. 16. The fracture tab 700 rotates to its fracture tab position two 714 so as to allow fluid contents 620 contained in the fluid containment area 610 to be discharged through cap fluid discharge opening 490. In this embodiment, the tube end 230 is a flexible material while the tube lower end 240 has less flexible material.

Figure 17A:
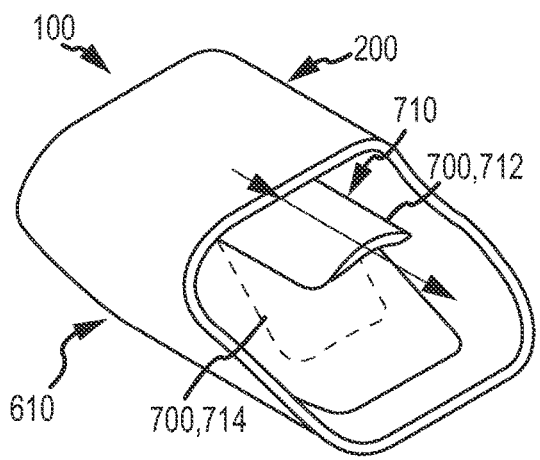
FIG. 17A is a partial cut-away view of the device with hinged/slot opening feature.
Figure 17B:
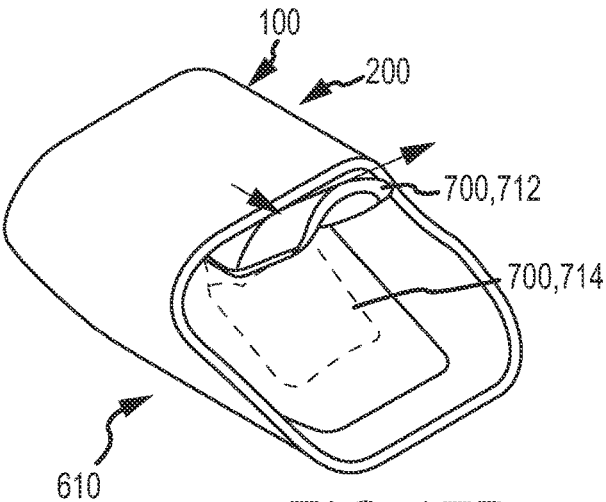
FIG. 17B is a partial cut-away view of the device with hinged/slot opening feature.
Figure 17C:
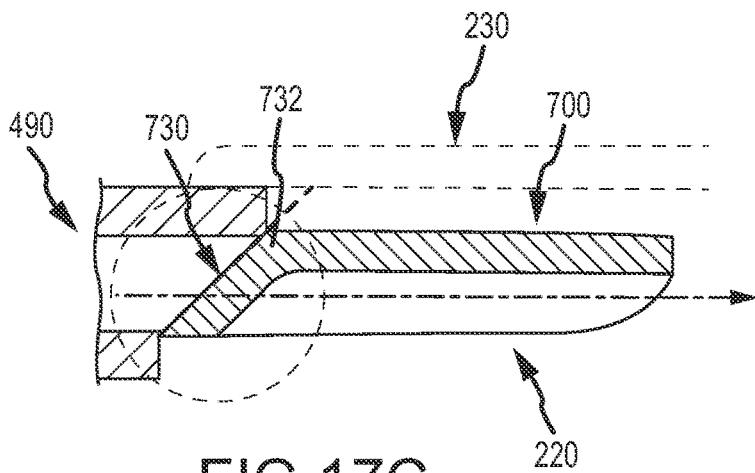
FIG. 17C is a cross-sectional side view of the hinged opening feature of FIG. 17A.
Figure 17D:
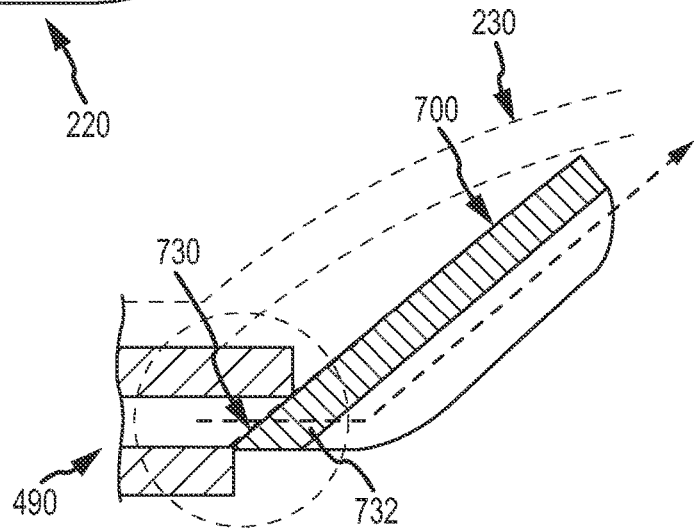
FIG. 17D is a cross-sectional side view of the hinged opening feature of FIG. 17B.

FIG. 17A is a partial cut-away view of the device with hinged/slot opening feature. FIG. 17B is a partial cut-away view of the device with hinged/slot opening feature. FIG. 17C is a cross-sectional side view of the hinged opening feature of FIG. 17A. FIG. 17D is a cross-sectional side view of the hinged opening feature of FIG. 17B.

Turning to FIG. 17A, the device 100 is depicted with tube 200, and fracture tab 700 in both its fracture tab position one 712 (or open position) and fracture tab position two 714. FIG. 17A depicts a configuration for the device 100 where the tube 200 is generally configured parallel with the fracture tab 700. FIG. 17B presents a configuration of the device 100 particularly suited for tube configurations in which tube 200 could be dome or clam-shelled shaped, thus requiring the open position of the fracture tab 700 to be projected at an angular orientation upwards as shown in FIG. 17B. FIG. 17B presents the device 100 with tube 200 and fracture tab 700, and both its fracture tab position one 712 and fracture tab position two 714. A close up of the fracture tab of FIG. 17A is shown in FIG. 17C. FIG. 17C presents a side cut-away view of the fracture tab 700 assembly in the configuration particularly suited in configurations of the device 100 in which the tube 200 is generally parallel with a fracture tab 700. FIG. 17C presents the device with a tube upper end 230, cap fluid discharge opening 490, fracture tab 700, and features of fracture tab 700 of fractured line 730 and fractured plane 732. When a user presses downward on the tube upper end 230, to engage the fracture tab 700, the fracture tab would rotate from its FIG. 17 closed position downward to allow fluid to escape from cap fluid discharge opening 490. FIG. 17D presents a close-up cross-sectional view of the tube upper end 230 of the embodiment of FIG. 17B. In FIG. 17D, the fracture tab 700 is shown with features of fracture line 730 and fracture plane 732. When a user engages tube upper end 230 in a downward manner the fracture tab 700 would rotate downward so as to open cap 490 to allow fluid to discharge.

FIGS. 17E-H depicts various views of the clam shell configuration. In FIG. 17E-I the hinge 700 configuration depicted in 17B would be particularly useful in clam-shelled or some configurations of tube 200.

FIGS. 18A-D depicts various top views of the device 100 in the clam shell or dome configuration with hinged fracture tab opening feature.

Figure 18A:
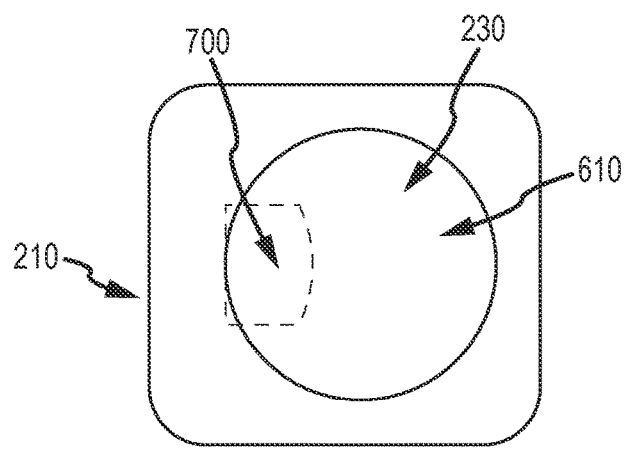
FIG. 18A is a top view of the device with hinged opening feature and with domed tube.
Figure 18B:
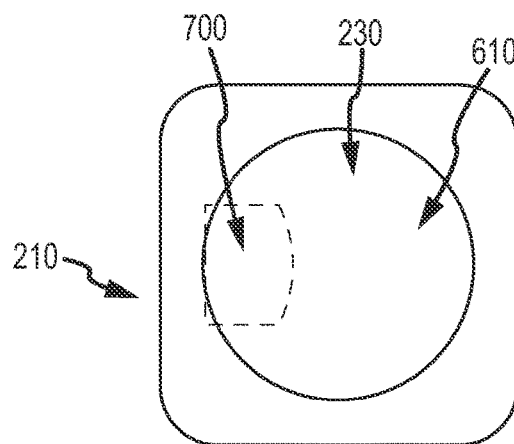
FIG. 18B is a top view of the device with hinged opening feature and with domed tube.
Figure 18C:
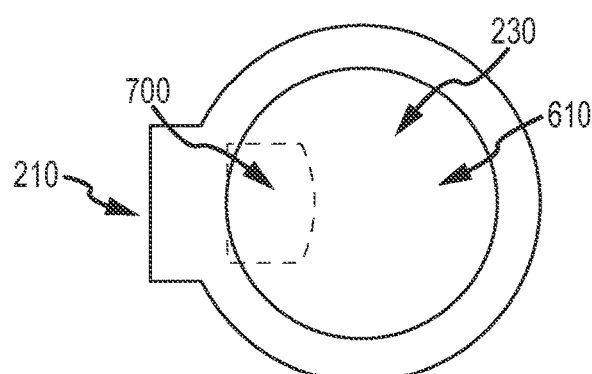
FIG. 18C is a top view of the device with hinged opening feature and with domed tube.
Figure 18D:
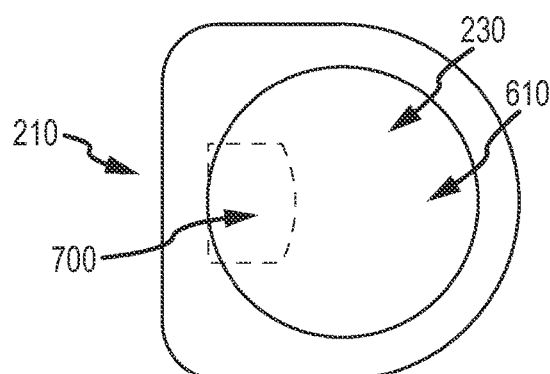
FIG. 18D is a top view of the device with hinged opening feature and with domed tube.
Figure 18E:
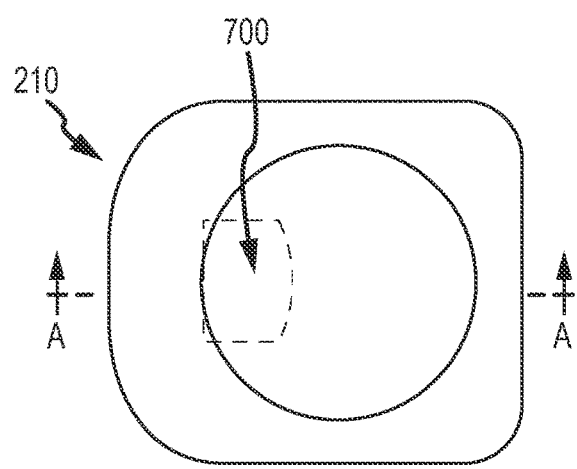
FIG. 18E is a top view of the device with hinged opening feature and with domed tube.
Figure 18F:
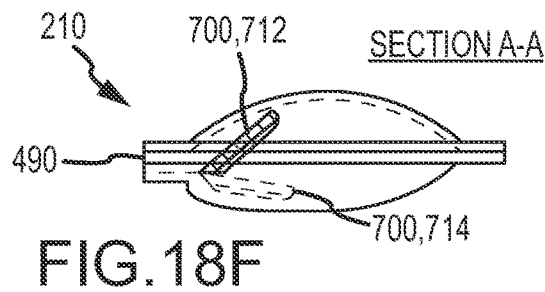
FIG. 18F is a side cross-sectional view of the device with hinged opening feature and with domed tube.
Figure 18I:
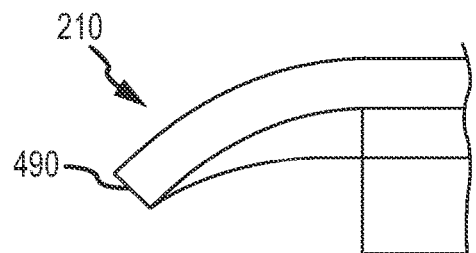
FIG. 18I is a magnified side-cross-sectional view of the device with hinged opening feature and with domed tube.
Figure 18G:
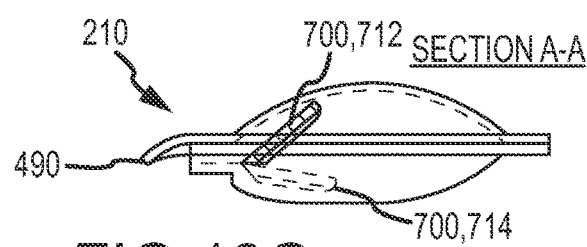
FIG. 18G is a side cross-sectional view of the device with hinged opening feature and with domed tube.
Figure 18H:
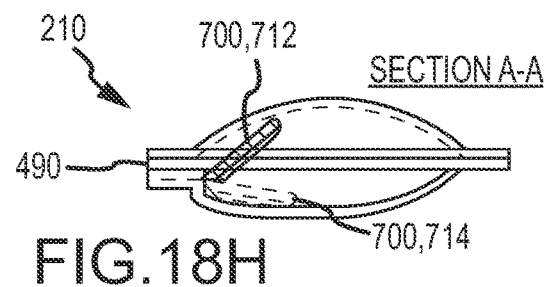
FIG. 18H is a side cross-sectional view of the device with hinged opening feature and with domed tube.

FIG. 18A depicts the tube first end 210 with tube upper end 230 and internal fracture tab 700. The dome shape of tube upper end 230 is slightly offset from the overall external structure of the device. In contrast in FIG. 18B the external structure of the device 100 in generally centered with the dome shape of the tube upper end 230. In FIG. 18C the device 100 is shown with tube first end 210, tube upper end 230, and fracture tab 700 with a slight elongation at the forward end tube first end 210. Lastly, FIG. 18D depicts another embodiment of the invention with tube first end 210 substantially elongated and with tube upper end 230 and fracture tab 700 identified.

Figure 19A:
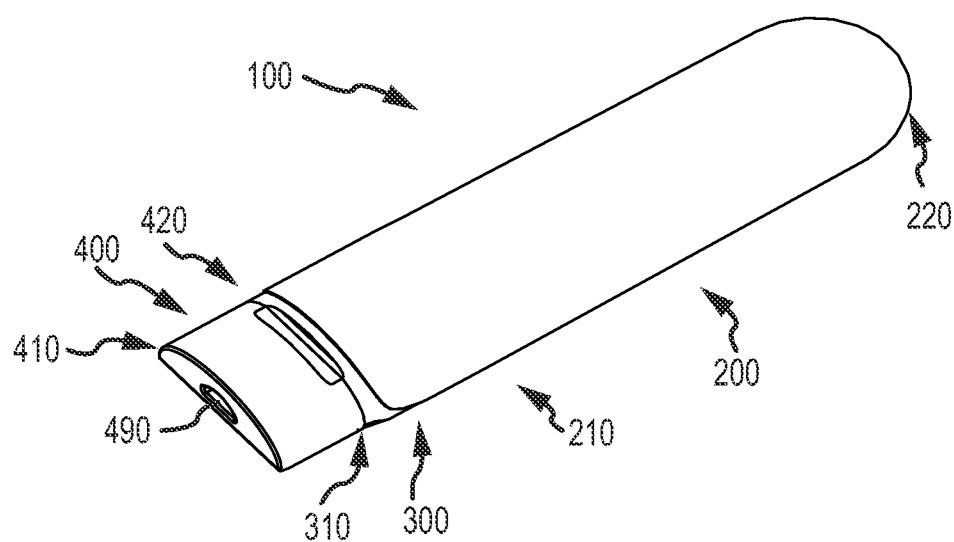
FIG. 19A is a perspective view of the device with slider opening and in the closed configuration.

In regard to FIG. 19A a perspective view of the device is provided. In this embodiment of the invention the device 100 is generally configured in an oval cylinder tube configuration with a slider opening feature. The device 100 generally includes a tube 200, a neck 300, and a cap 400. The tube section 200 includes a tube first end 210 and a tube second end 220. The neck 300 includes a neck first end 310. The cap section 400 of the device 100 includes a cap first end 410 and a cap second end 420. Furthermore, the cap 400 includes a cap fluid discharge opening 490. FIG. 19A depicts the device 100 in the closed configuration, that is, unable to discharge its contents.

Figure 19B:
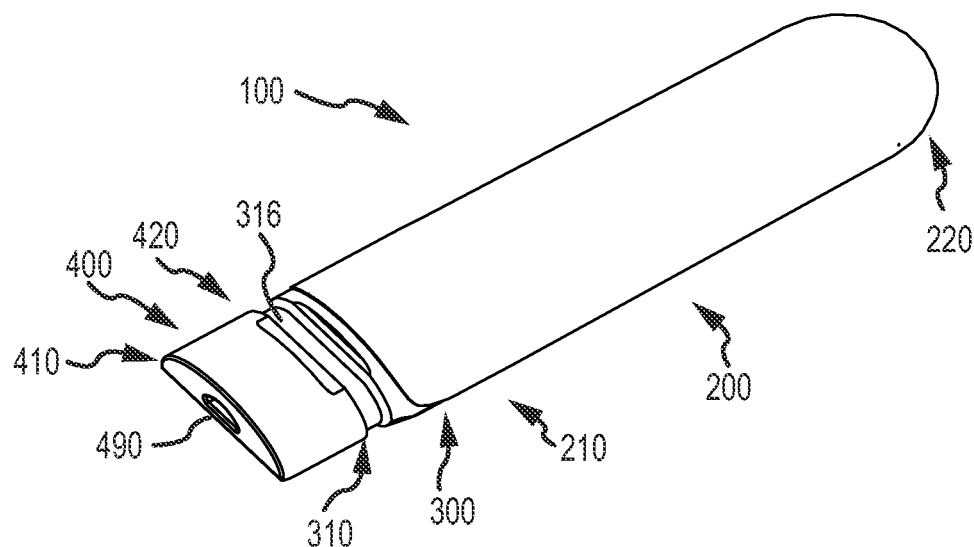
FIG. 19B is a perspective view of the device with slider opening and in the open configuration.

In regard to FIG. 19B a perspective view of the device is provided. In this embodiment of the invention the device 100 is generally configured in an oval cylinder tube configuration with a slider opening feature. The device 100 generally includes a tube 200, a neck 300, and a cap 400.

The tube section 200 includes a tube first end 210 and a tube second end 220. The neck 300 includes a neck first end 310 and neck extended channel 316. The cap section 400 of the device 100 includes a cap first end 410 and a cap second end 420. Furthermore, the cap 400 includes a cap fluid discharge opening 490. FIG. 19B depicts the device 100 in the open configuration, that is, able to discharge its contents.

Figure 19C:
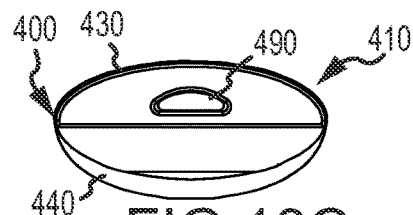
FIG. 19C is a front view of the device with slider opening.

In FIG. 19C the cap 400 is shown with a cap first end 410, cap first exterior surface 430, a cap second exterior surface 440, cap fluid discharge opening 490.

Figure 19D:
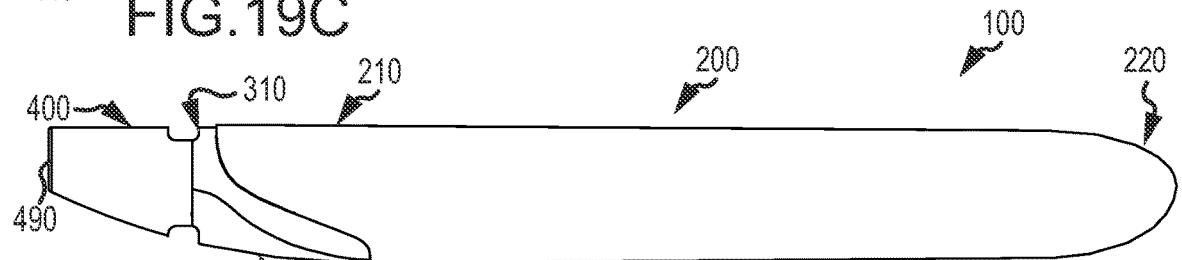
FIG. 19D is a side view of the device with slider opening and in the closed configuration.
Figure 19E:
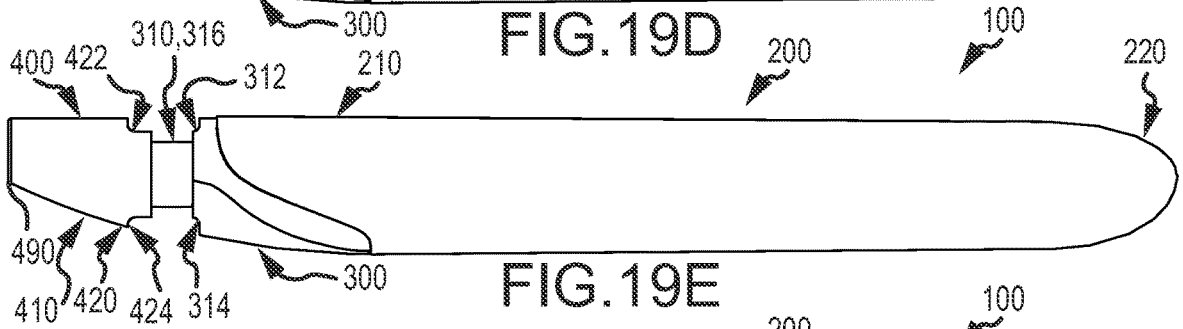
FIG. 19E is a side view of the device with slider opening and in the open configuration.

FIGS. 19D and 19E illustrate side views of the device 100 in closed configuration and open configuration, respectfully.

FIG. 19C presents the device 100 with tube 200, neck 300 and cap 400. Also shown are cap first end 210, cap second end 220, neck first end 310, and cap fluid discharge opening 490. FIG. 19D presents the device 100 with tube 200, neck 300 and cap 400. Also shown are cap first end 210, cap second end 220, neck first end 310, and cap fluid discharge opening 490. In addition, neck extended channel 316, neck indent upper 312, neck indent lower 314, cap indent upper 422, and cap indent lower 424 are shown. Cap first end 410 and cap second end 420 are also provided.

Figure 19F:
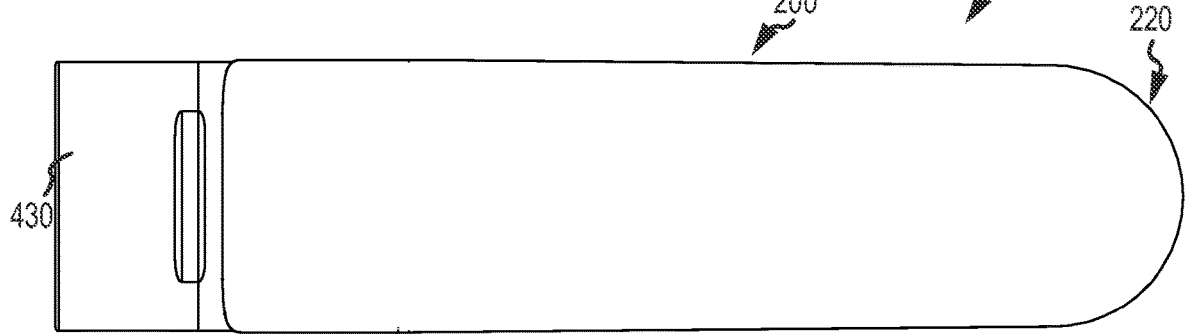
FIG. 19F is a top view of the device with slider opening and in the open configuration.
Figure 19G:
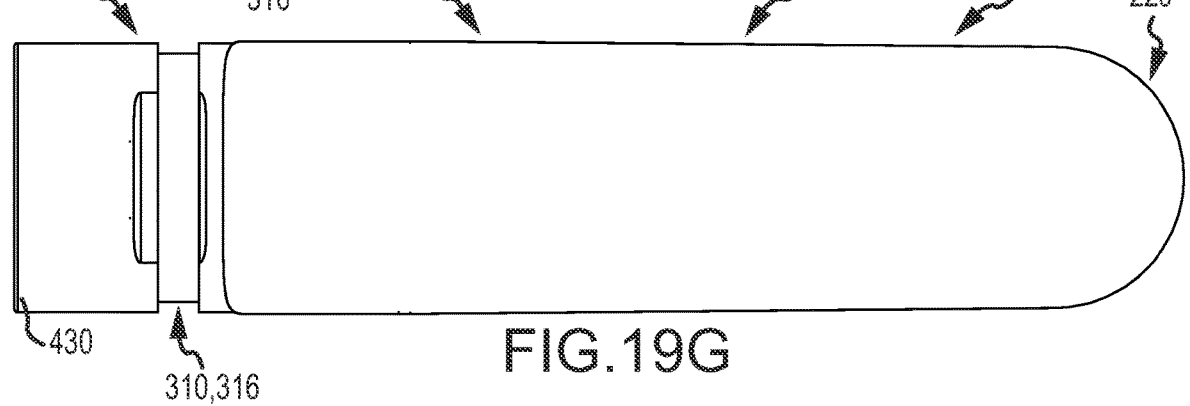
FIG. 19G is a top view of the device with slider opening and in the open configuration.

FIGS. 19F and 19G illustrate top views of the device 100 in closed configuration and open configuration, respectfully.

FIG. 19F presents the device 100 with tube 200, neck 300, cap 400, neck first end 310, and cap first exterior surface 430.

FIG. 19G presents the device 100 with tube 200, neck 300, cap 400, neck first end 310, and cap first exterior surface 430. Also shown is neck extended channel 316.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for administration of a predetermined amount of fluid, comprising:

providing an apparatus to a desired treatment situs, the apparatus comprising: a tube portion configured to hold the predetermined amount of fluid; a neck portion comprising a hermetic seal coupled to the tube portion; and a cap portion having a cap first end, a cap second end, and at least one portion with a substantially cylindrical geometry when viewed from a front view, the cap portion arranged over a portion of the neck portion, said cap first end extending from said cap second end, the cap first end having a surface that is orthogonal to a central axis of the cap portion, said cap first end having a fluid discharge opening in the orthogonal surface, a first region of the cap portion extending at an angle from the cap first end to the cap second end where the first region has a portion with a substantially planar surface, said cap portion coupled to the tube portion, the hermetic seal configured to permit a shelf life of one or more years for the fluid, wherein the cap portion is configured to move from a closed position to an open position, and wherein the cap portion is not detachable from the neck portion of the apparatus; and positing the cap portion at the desired treatment situs; and moving the cap portion from the closed position to the open position in order to permit discharge of the fluid.

2. The method of claim 1, wherein the desired treatment situs is an oral cavity.

3. The method of claim 1, wherein the desired treatment situs is a predetermined location of a body, an animal, a substrate, an article, or a combination thereof.

4. The method of claim 1, wherein the fluid comprises a pharmacological agent.

5. The method of claim 4, wherein the pharmacological agent is selected from the group consisting of acetaminophen, ibuprofen, antacid, cough medicine, cold medicine, and combinations thereof.

6. An improved method for administration of a predetermined volume of fluid, comprising:

providing an apparatus to a desired treatment situs, the apparatus comprising: a tube portion configured to hold the predetermined volume of fluid; a neck portion comprising a hermetic seal coupled to the tube portion; and a cap portion having a cap first end, a cap second end and at least one portion with a substantially cylindrical geometry when viewed from a front view, the cap portion arranged over a portion of the neck portion, said cap first end extending from said cap second end, the cap first end having a surface that is orthogonal to a central axis of the cap portion, the cap first end having a fluid discharge opening arranged as an aperture in the orthogonal surface, a first region of the cap portion extending at an angle from the cap first end to the cap second end where the first region has a portion with a substantially planar surface configured to allow for spreading of the fluid, said cap portion coupled to the tube portion, the hermetic seal configured to permit a shelf life of one or more years for the fluid, wherein the cap portion is configured to move from a closed position to an open position, and wherein the cap portion is not detachable from the neck portion of the apparatus;

positioning the cap portion adjacent to the desired treatment situs; and moving the cap portion from the closed position to the open position with manual pressure of a thumb or a finger to release the predetermined volume of fluid.

7. The method of claim 6, wherein the treatment situs is an oral cavity.

8. The method of claim 6, wherein the treatment situs is a predetermined location of a body.

9. The method of claim 8, wherein the fluid comprises a pharmacological agent.

10. The method of claim 8, wherein the pharmacological agent is selected from the group consisting of acetaminophen, ibuprofen, antacid, cough medicine, cold medicine, and combinations thereof.

11. A method for administration of a predetermined volume of a fluid, comprising:

providing an apparatus to a desired treatment situs, the apparatus comprising: a tube portion configured to hold the predetermined volume of fluid; a neck portion comprising a hermetic seal coupled to the tube portion; and a cap portion having a cap first end, a cap second end and at least one portion with a substantially cylindrical geometry when viewed from a front view, the cap portion arranged over a portion of the neck portion, said cap first end extending from said cap second end, the cap first end having a surface that is orthogonal to a central axis of the cap portion, the cap first end having a fluid discharge opening arranged as an aperture in the surface, a first region of the cap portion extending at an angle from the cap first end to the cap second end where the first region has a portion with a substantially planar surface configured to allow for spreading of the fluid, said cap portion coupled to the tube portion, the hermetic seal configured to permit a shelf life of one or more years for the fluid, wherein the cap portion is configured to move from a closed position to an open position, and wherein the cap portion is not detachable from the neck portion of the apparatus;

positioning the cap portion in an oral cavity of a user; and moving the cap portion from the closed position to the open position with manual pressure of a thumb or a finger to release the predetermined volume of fluid, wherein the predetermined volume is less than 10 mL.

12. The method of claim 11, wherein the fluid comprises a pharmacological agent selected from the group consisting of acetaminophen, ibuprofen, antacid, cough medicine, cold medicine, and combinations thereof.

* * * * *